United States Patent
Carvalho et al.

[11] Patent Number: 5,972,307
[45] Date of Patent: Oct. 26, 1999

[54] DICHELANTS

[75] Inventors: Joan Carvalho, Mountain View; Alan D. Watson, Campbell; Jere D. Fellmann, Livermore; Michael Koo, San Jose, all of Calif.

[73] Assignee: Nycomed Salutar, Inc., Wayne, Pa.

[21] Appl. No.: 08/898,376

[22] Filed: Jul. 22, 1997

Related U.S. Application Data

[60] Division of application No. 08/226,760, Apr. 12, 1994, Pat. No. 5,650,133, which is a continuation-in-part of application No. 08/086,996, Jul. 7, 1993, Pat. No. 5,446,145, which is a continuation-in-part of application No. 07/468,107, Jan. 19, 1990, Pat. No. 5,281,704, said application No. 08/226,760, is a continuation-in-part of application No. 07/885,028, Jun. 12, 1992, abandoned, which is a continuation-in-part of application No. 07/468,107.

[30] Foreign Application Priority Data

Oct. 1, 1993 [GB] United Kingdom ............... 9320277

[51] Int. Cl.$^6$ .................. A61K 51/04; A61B 5/055; C07F 5/00; C07D 225/00

[52] U.S. Cl. .................. 424/1.65; 424/9.363; 424/9.42; 534/10; 534/15; 540/460; 540/465; 540/474

[58] Field of Search .................. 424/1.65, 1.69, 424/9.36, 9.361, 9.363, 9.42; 540/465, 460, 461, 474; 544/69, 168, 169; 562/565; 560/169; 534/10, 14, 15; 536/17.1, 17.4, 17.9; 530/405

[56] References Cited

U.S. PATENT DOCUMENTS

| | | | |
|---|---|---|---|
| 4,217,436 | 8/1980 | Richter et al. | 528/45 |
| 5,049,667 | 9/1991 | Schaefer et al. | 540/474 |
| 5,275,801 | 1/1994 | Niedballa et al. | 424/9.362 |
| 5,334,371 | 8/1994 | Gries et al. | 424/9.34 |
| 5,446,145 | 8/1995 | Love et al. | 540/465 |

FOREIGN PATENT DOCUMENTS

| | | |
|---|---|---|
| A 0 233 619 | 8/1987 | European Pat. Off. |
| A 0 255 471 | 2/1988 | European Pat. Off. |
| A 0 305 320 | 3/1989 | European Pat. Off. |
| A 0 331 616 | 9/1989 | European Pat. Off. |
| A 0 485 045 | 5/1992 | European Pat. Off. |
| A 62 077 374 | 4/1987 | Japan. |
| WO A 90/12050 | 10/1990 | WIPO. |
| WO A 91/05762 | 5/1991 | WIPO. |
| WO A 95/07270 | 3/1995 | WIPO. |

*Primary Examiner*—Jose' G. Dees
*Assistant Examiner*—Michael G. Hartley
*Attorney, Agent, or Firm*—Fish & Richardson P.C.

[57] ABSTRACT

This invention relates to dichelants, in particular compounds having two macrocyclic chelant groups linked by a bridge containing an ester or amide bond, especially compounds of formula Vb

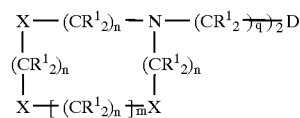

(wherein each X which may be the same or different is NZ, O or S, at least two Xs being NZ;

each Z is a group $R^1$ or a group $CR^1_2Y$, at least one Z, and preferably 2 or 3 Zs, on each macrocyclic ring being a group $CR^1_2Y$;

each Y is a group $CO_2H$, $PO_3H$, $SO_3H$, $CONR^1_2$, $CON(OR^1)R^1$, CNS or $CONR^1NR^1_2$, preferably COOH;

m is 0 or 1 or 2, preferably 1; each n is 2 or 3, preferably 2; q is 1 or 2, preferably 1;

each $R^1$ which may be the same or different is a hydrogen atom or an alkyl group optionally substituted by one or more hydroxy and/or alkoxy groups;

and D is a bridging group having a molecular weight of less than 1000, preferably less than 500, joining two macrocyclic rings via at least one amide or ester bond) and salts and metal chelates thereof.

5 Claims, No Drawings

DICHELANTS

This application is a divisional of Ser. No. 08/226,760, filed Apr. 12, 1994, now U.S. Pat. No. 5,650,133, which is a continuation-in-part of Ser. No. 08/086,996, filed Jul. 7, 1993, now U.S. Pat. No. 5,446,145, which is a continuation-in-part of Ser. No. 07/468,107, filed Jan. 19, 1990, now U.S. Pat. No. 5,281,704, said Ser. No. 08/226,760, filed Apr. 12, 1994, is a continuation-in-part of Ser. No. 07/885,028, filed Jun. 12, 1992, now abandoned, which is a continuation-in-part of Ser. No. 07/468,107, filed Jan. 19, 1990, now U.S. Pat. No. 5,281,704.

FIELD OF THE INVENTION

The present invention relates to dichelants, that is chelating agents capable of complexing two metal ions simultaneously, and to chelates and salts thereof and their use in diagnostic and therapeutic compositions, especially as contrast enhancing agents in diagnostic medical imaging.

BACKGROUND OF THE INVENTION

The medical use of chelants is now well established, for example as stabilisers for pharmaceutical preparations, as antidotes for poisonous heavy metal species, as carriers for diagnostically or therapeutically useful metal ions, for example in contrast media for use in magnetic resonance, X-ray or ultrasound imaging or in scintigraphy.

For such diagnostic agents, it is generally important that the chelate complexes should be stable both kinetically and thermodynamically and for this reason there has been much interest in the macrocyclic polyamine-based chelates, in particular DOTA and its derivatives and analogues, which form very stable complexes with the lanthanide metal ions such as gadolinium and dysprosium which are favoured diagnostic metal ions for magnetic resonance imaging due to their relatively large effects on the relaxation times (e.g. $T_1$ and $T_2^*$) of neighbouring water protons.

The paramagnetic lanthanide metal ions useful as MR imaging contrast agents are relatively toxic and for clinical use must be administered in a form which allows little or no release of the metal for subsequent biological uptake and retention. For this reason, from the early years of MR contrast agents, the use of stable chelate complexes has been proposed. Thus the first commercial lanthanide based MR imaging contrast agent, Magnevist, contained GdDTPA, a complex with a high stability constant which following parenteral administration is excreted relatively rapidly by glomerular filtration with the gadolinium still in the chelate complex.

GdDOTA has an even higher $pK_{ML}$ and thus was also a prime candidate for consideration as an MR imaging contrast agent. DOTA (1,4,7,10-tetraazacyclododecane-N,N',N",N"'-tetraacetic acid) and HPDO3A (1-(2-hydroxypropyl)-4,7,10-tetraazacyclododecane-N,N',N"-triacetic acid) have indeed been proposed as chelants for MR imaging contrast agents and GdDOTA and GdHPDO3A have been commercially developed by companies active in this field.

The lanthanide metals generally have a stable +3 oxidation state and DOTA with its four carboxylic acid groups results in a charged complex, i.e. GdDOTA⁻, requiring a counterion. Analogous uncharged complexes may be produced by eliminating one of DOTA's nitrogen-attached carboxymethyl groups or by replacing it by a non-ionizing group, i.e. by using a chelant such as DO3A (1,4,7,10-tetraazacyclododecane-N,N',N"-triacetic acid) or HPDO3A.

Contrast media based on such non-ionic, or overall charge neutral, complexes have lower osmolalities for a given metal ion concentration and can demonstrate other improved properties relative to the analogous charged complexes. Moreover, the ring nitrogen "freed" by removal of the carboxymethyl group in moving from DOTA to DO3A can of course be substituted by groups which can act to enhance the hydrophilicity or lipophilicity or other biodistribution affecting properties of the chelate.

Recently, there has been growing interest in the use of chelants capable of chelating more than one metal ion per chelant molecule as carriers for paramagnetic or heavy metal ions for MR or X-ray imaging contrast agents. These polychelants offer several advantages over the monochelants such as DTPA, DO3A or DOTA. Thus for example, the osmolality at a given metal concentration can be reduced still further, the simultaneous delivery of a plurality of metal ions to a target site can be facilitated, and more efficient contrast agents can be produced.

Polychelants range from dichelants through oligochelants to true polychelants having perhaps hundreds of chelant moieties per molecule. Many such compounds have been described but there is still a need for polychelants, and in particular oligochelants and especially dichelants, having improved properties in terms for example of relaxivity, stability, biodistribution, biotolerability, viscosity, solubility and osmolality.

Particular macrocyclic dichelants described in the literature include the DO3A dimers of formula II, III and IV whose preparation has been described by Schering AG in EP-A-255471 and EP-A-485045 (U.S. Pat. No. 5,277,895) and elsewhere.

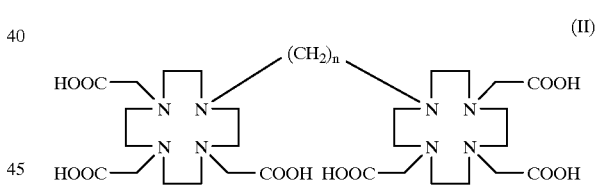

(II)

(where n=3, 5 or 6)

(described by Schering AG in EP-A-255471 and in a poster presented at the European Congress of NMR in Medicine and Biology at Strasbourg in May 1990)

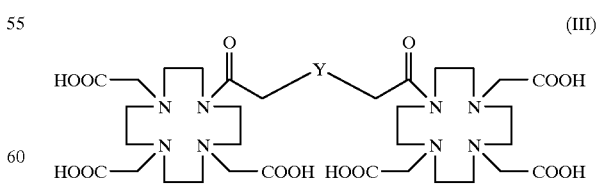

(III)

(where Y is [—N(CH$_2$COOH)CH$_2$CH$_2$N(CH$_2$COOH)CH$_2$CH$_2$N(CH$_2$COOH)⁻]$_a$ and a=0 or 1)

(described by Schering AG in EP-A-255471)

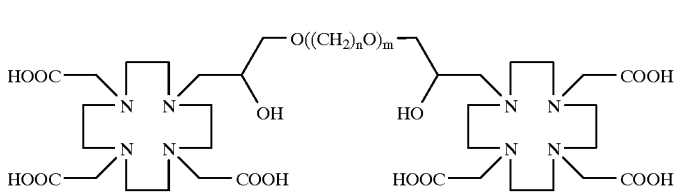

(IV)

(where n=2 or 4 and m=0 or 1)
(described by Schering AG in EP-A-485045 (U.S. Pat. No. 5,277,895)).

All of these macrocyclic chelant dimers have the general formula DO3A'-L-DO3A' where DO3A' is a ring nitrogen deprotonated DO3A residue and L is a linker group.

With lanthanides such as gadolinium, these macrocyclic dimers will produce non-ionic dichelates and these compounds have been found to possess high relaxivity. Thus for example the Tl relaxivities of the bisgadolinium chelates of the compounds of formula II are almost double the Tl relaxivity of GdDO3A.

SUMMARY OF THE INVENTION

We have now found that dichelant compounds having improved properties are produced if the linker groups incorporate ester or amide functionalities, and especially where the linkers comprise carbonyl-attached alkylene groups in which two or more of the methylene groups are replaced by nitrogen or oxygen atoms.

Thus viewed from one aspect the invention provides a polychelant of formula Va

A—L—A (Va)

(where each A which may be the same or different is a macrocyclic chelant moiety and L is a linker moiety incorporating at least one amide or ester bond in the atom chain linking the two chelant groups A) or a salt or chelate thereof.

Conveniently the A—L bonds in the compounds of formula Va will be of formula A'—CO—X*—L' where X* is oxygen or a secondary or tertiary or ring nitrogen, ie. the carbonyl function in the amide or ester bond will conveniently be to the chelant side of the bond.

Thus linker compounds useful for the production of dimeric chelants ALA include, but are not limited to diamine or diol compounds such as 1,2-diaminoethane, 1,3-diaminopropane, 1,4-diaminobutane, N,N'-dimethyl-1,2-diaminoethane, N,N'-dimethyl-1,3-diaminopropane, 1,4-diaminocyclohexane, 1,4-phenylenediamine, diethylenetriamine, triethylenetetraamine, piperazine, 1,4-diazacycloheptane, 1,5-diamino-3-oxapentane, 1,8-diamino-3,6-dioxaoctane, 1,11-diamino-3,6,9-trioxaundecane, 1,7-diaza-4,10,13-trioxapentadecane and 2,2-dimethyl-1,3-propanediol.

Preferably the compounds of the invention are polychelants of formula Vb

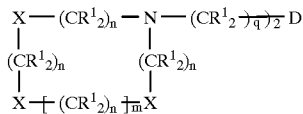

(Vb)

(wherein each X which may be the same or different is NZ, O or S, at least two Xs being NZ;

each Z is a group $R^1$ or a group $CR^1_2Y$, at least one Z, and preferably 2 or 3 Zs, on each macrocyclic ring being a group $CR^1_2Y$;

each Y is a group $CO_2H$, $PO_3H$, $SO_3H$, $CONR^1_2$, $CON(OR^1)R^1$, CNS or $CONR^1NR^1_2$, preferably COOH;

m is 0 or 1 or 2, preferably 1; each n is 2 or 3, preferably 2; q is 1 or 2, preferably 1;

each $R^1$ which may be the same or different is a hydrogen atom or an alkyl group optionally substituted by one or more hydroxy and/or alkoxy groups;

and D is a bridging group having a molecular weight of less than 1000, preferably less than 500, joining two macrocyclic rings via at least one amide or ester bond) and salts and metal chelates thereof.

Viewed from a further aspect, the present invention provides a diagnostic or therapeutic agent comprising a metal chelate, whereof the chelating entity is the residue of a compound according to the present invention, together with at least one pharmaceutical or veterinary carrier or excipient, or adapted for formulation therewith or for inclusion in a pharmaceutical formulation for human or veterinary use Viewed from another aspect, the present invention provides a detoxification agent comprising a chelating agent according to the invention in the form of a weak complex or salt with a physiologically acceptable counterion, together with at least one pharmaceutical or veterinary carrier or excipient, or adapted for formulation therewith or for inclusion in a pharmaceutical formulation for human or veterinary use.

Viewed from a further aspect, the present invention provides a method of generating enhanced images of the human or non-human animal body, which method comprises administering to said body an effective amount of a diagnostic agent comprising a metal chelate of compound of formula V (ie. Va or Vb), or a salt thereof, and generating an image of at least part of said body to which said chelate distributes, wherein said metal is paramagnetic, radioactive or X-ray opaque.

Viewed from a further aspect, the present invention provides a method of radiotherapy practised on the human or non-human animal body, which method comprises administering to said body an effective amount of a chelate of a radioactive metal species with a chelating agent of formula V, or a salt thereof.

Viewed from a further aspect, the present invention provides a method of heavy metal detoxification practised on the human or non-human animal body, which method comprises administering to said body an effective amount of a chelating agent of formula V or a physiologically tolerable salt or weak complex thereof.

Viewed from a still further aspect, the present invention provides a process for the preparation of the metal chelates of the invention which process comprises admixing in a solvent a compound of formula V or a salt (e.g. the sodium salt) or chelate thereof together with an at least sparingly soluble compound of said metal, for example a chloride., oxide, acetate or carbonate.

DETAILED DESCRIPTION

In the compounds of the invention, the macrocyclic

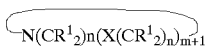

rings preferably have 9 to 14 ring atoms, the ring heteroatoms especially preferably being either all nitrogen or being one oxygen and three nitrogens. The alkylene ring segments $(CR^1_2)_n$ preferably are all $(CR^1_2)_2$ groups or in the case of an $N_4$ macrocycle the alkylene segments may alternatively be alternating $(CR^1_2)_3$ and $(CR^1_2)_2$ groups. Thus the preferred macrocyclic skeletons are those of formulae VI

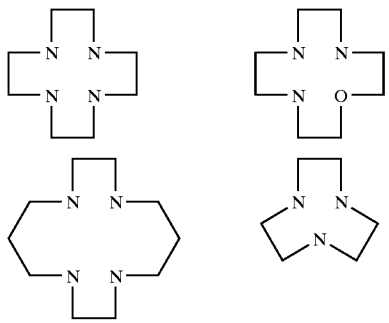 (VI)

The bridging group D is conveniently a group of formula

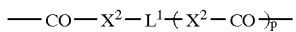

where p is 0 or 1, $X^2$ is O or $NR^2$, $R^2$ is a hydrogen atom or a hydroxy, $OR^1$ or $NR^1_2$ group or an alkyl group optionally interrupted by oxygen, sulphur or nitrogen atoms or by carbonyl or aryl groups and optionally substituted by hydroxyl, amine or aryl groups, or $R^2$ contains a functional group for attachment to a biomolecule or macromolecule, or two $R^2$ groups together form a bridging linker group, e.g. a group $L^1$, and $L^1$ which provides a chain of at least two atoms linking two $X^2$ groups or at least one atom linking an $X^2$ group and a $(CR^1_2)_q$ moiety, is a straight chain, branched or cyclic alkylene group or a combination of such groups, optionally substituted and optionally being interrupted by oxygen, sulphur or nitrogen atoms or by aryl or carbonyl groups.

The linker group $L^1$ will preferably be a linear, branched or cyclic alkylene group or a combination thereof or a combination of arylene and alkylene groups, for example providing a linking backbone 1 to 50 atoms long but preferably 2 to 25, and especially 2 to 10 atoms long in total on any one unbranched segment. The carbon backbone in such linker groups may be interrupted by heteroatoms such as nitrogen, oxygen and sulphur, and may carry bridging groups, thereby creating homo- or heterocyclic rings within the linker group. Where this occurs, the rings created will preferably be 3 to 12, especially 5 to 8 and, particularly, 6 membered rings. Moreover the rings and the linear segments of the linker group may optionally be unsaturated and may optionally carry one or more substituents selected from alkyl, hydroxy, alkoxy, amine, aryl and substituted aryl groups as well as non-hydrogen $R^1$ groups or additional chelating groups, eg. Y groups especially carbonyl and $SO_3H$ groups, and groups such as for example long chain (eg. $C_{10-20}$) alkyl, aryl or polyaryl groups which are suitable for liposomal incorporation of the compound of formula V or groups, such as isothiocyanate groups, for attachment of the compound of formula V to a biomolecule, polymer, dendrimer or other macromolecule, for example to create a bifunctional chelant.

The bridging group D in the compounds of the invention may, as indicated above, serve to link together two chelant moieties, thereby holding together the dichelate structure. Besides filling this role as linker or spacer of chelant sites, the bridging group can be so selected as to yield a product having other desired characteristics. For example it is possible to increase hydrophilicity, lipophilicity, or tissue specificity of the end product by attaching to or incorporating within the bridging group, groups which are hydrophilic, lipophilic, or tissue targeting. In this way, the overall charge of the chelate structure, or the overall lipophilicity, or tissue targeting can be controlled.

In the compounds of formula V, alkyl moieties preferably have 1 to 6, especially 1 to 4 carbon atoms unless otherwise specified, and aryl moieties are preferably phenyl groups.

Particularly preferred compounds of formula V include those of formula VII

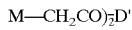 (VII)

where M is a nitrogen attached triaza, tetraaza, triazaoxa or triazathia-cycloalkane of formula VI having at least one and preferably two ring nitrogens substituted by $CH_2COOH$ groups and having any remaining ring nitrogen substituted by a group $R^3$, M preferably being a group of formula VI having two or more, preferably three, ring heteroatoms substituted by $CH_2COOH$ groups; $R^3$ (which for tetraheteroatom rings is preferably at the ring heteroatom remote from the ring attachment nitrogen) is a hydrogen atom, or an alkyl group optionally mono or polysubstituted by hydroxyl or alkoxy groups (eg. hydroxyalkyl, polyhydroxyalkyl, alkoxyalkyl, polyalkoxyalkyl, hydroxyalkoxyalkyl, hydroxypolyalkoxyalkyl, polyethylene glycol etc.) and optionally interrupted by arylene or substituted arylene groups; and CO—D'—CO is a bridging group D as discussed above.

Preferred bridging groups D in the dichelant compounds of the invention include those of the formulae:

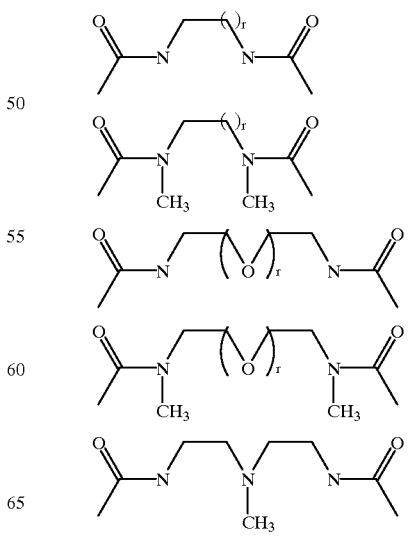

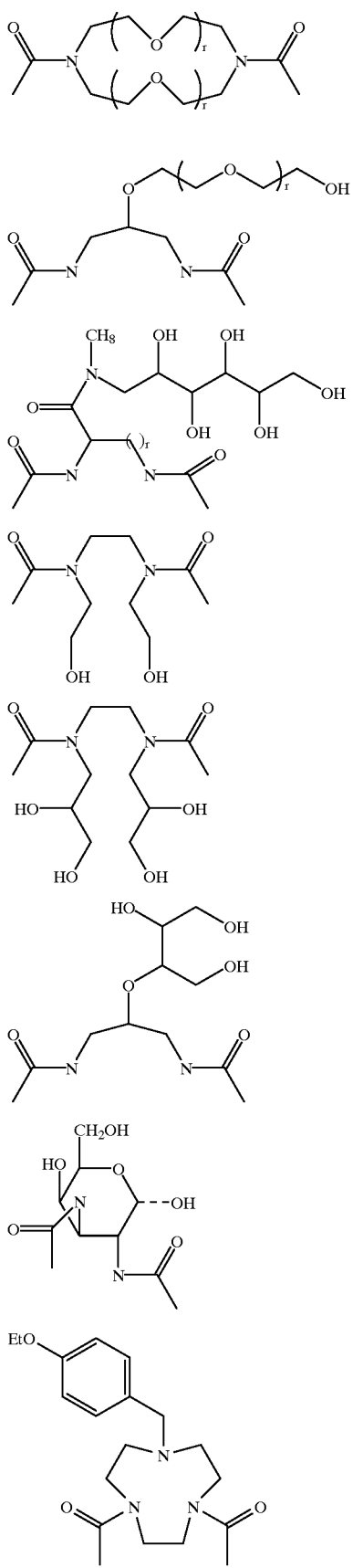
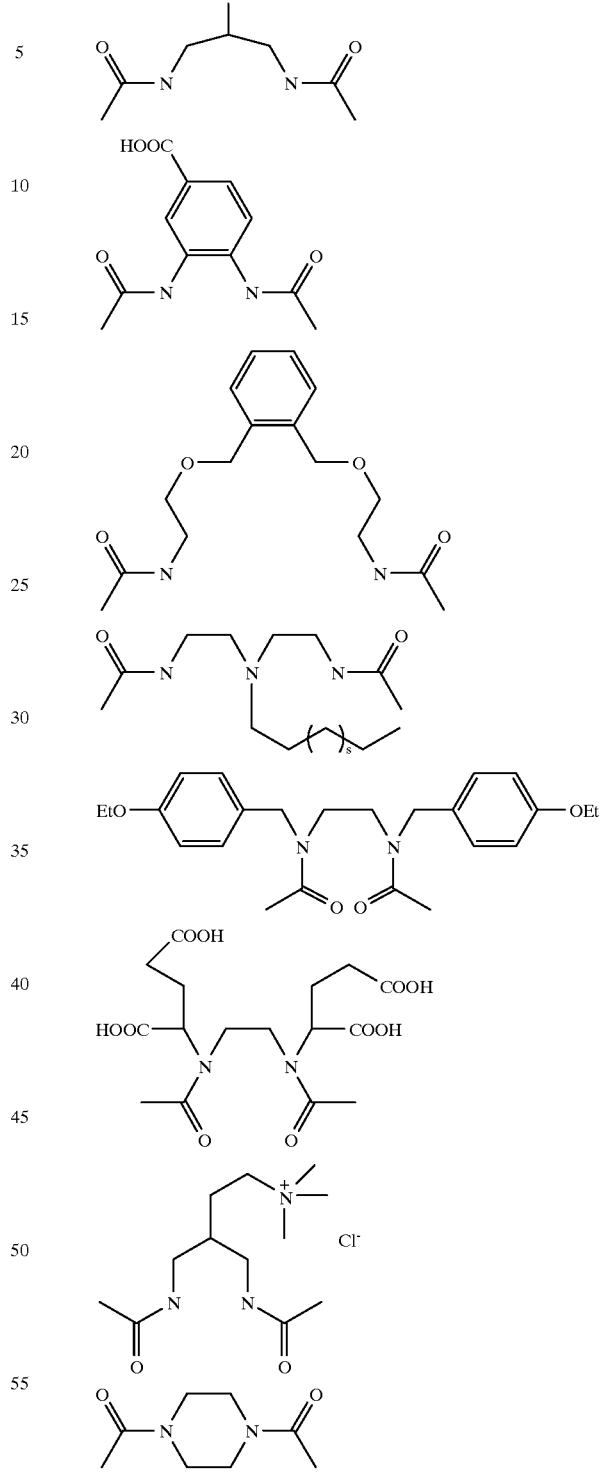
where r is an integer having a value of 1 to 6, especially 1, 2 or 3, and s is an integer having a value of 1 to 20, especially 1 to 15.
Especially preferred are bridging groups containing ether oxygens, for example $COOCH_2CH_2OCH_2CH_2NHCH_2CH_2OCH_2CH_2OCO$, as these may be associated with particularly low toxicity.

Preferred compounds according to the invention also include the polyhydroxylated dichelants, e.g. where D or $R^1$ groups are hydroxylated, as they can present a better toxicity profile than their non-hydroxylated counterparts. Lipophilic analogs are also of interest due to the potential for increased liver uptake; moreover the long chain lipophilic analogs have the ability to be incorporated into liposomes for use as blood pool agents and for targetted delivery to specific organs or tissues. Indeed chelate compounds according to the invention, in particular the lipophilic analogs, are of particular interest as blood pool agents where they exhibit prolonged plasma half lifes.

The compounds of the invention may be prepared by conventional synthetic techniques, conveniently starting from the corresponding N-unsubstituted or N-carboxymethylated polyazacycloalkanes, condensing these to a bifunctional linker molecule, generally after protection of one or more of the ring nitrogens or N-carboxymethyl groups, followed by deprotection and if required introduction of functional groups at the ring nitrogens.

Where the dichelant is asymmetrical, it can of course be constructed by conjugating one macrocycle to a monoprotected bifunctional linker molecule, deprotecting, and conjugating a second macrocycle to the macrocycle-linker intermediate. For such purposes, the bifunctional linker molecule may of course itself be asymmetric to allow one end to conjugate directly to a macrocycle ring nitrogen and the other to conjugate to a macrocycle side chain, e.g. a carboxymethyl group or a reactive derivative thereof.

Thus viewed from a further aspect the invention also provides a process for the preparation of the compounds of the invention, said process comprising at least one of the following steps:

(a) reacting a compound of formula V wherein at least one group X is a group NH, with a compound of formula VIII.

(VIII)

(where Lv is a displaceable leaving group, for example a halogen atom or a substituted sulphonyloxy group, such as chlorine, bromine, iodine, methanesulphonyloxy, phenysulphonyloxy or p-toluenesulphonyloxy groups) and $R^4$ is a group $CR^1{}_2Y$ or group $R^1$ other than hydrogen);

(b) reacting compounds of formulae X and/or XI

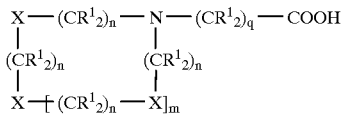

(wherein X, $R^1$, n, q and m are as hereinbefore defined) or an activated derivative, e.g. halide, thereof with a linker molecule of formula IX

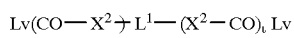

(IX)

(wherein $X^2$ and $L^1$ are as hereinbefore defined, t is 0 or 1, and each Lv is a displaceable leaving group, one optionally being protected prior to conjugation of the second compound of formula X or XI);

(c) metallating or transmetallating a compound of formula V or a chelate thereof;

(d) converting a compound of formula V or a chelate thereof into a base or acid addition salt thereof or converting a salt into the free acid or base; and (e) performing at least one of steps (a) to (c) above using reagents with protected functional groups and subsequently removing the protecting groups.

The starting compounds of formulae VIII, IX, X and XI are either known from the literature or can be produced by conventional synthetic techniques. The starting compounds of formula VIII used in step (a) can be prepared by the process of step (b).

As indicated above, during the reaction, functional groups present in the starting materials but not involved in the particular process steps may be protected, for example to avoid unwanted substitution or polymerisation. Conventional protection and deprotection techniques may be used (see for example "Protective Groups in Organic Synthesis" by T. W. Greene, Wiley-Interscience, NY, 1981 and "Protective Groups in Organic Chemistry" by J F W McOmie, Plenum, London, 1973). Suitable protecting groups for carboxyl groups include ester functions, for ring nitrogens alkyl, borane or organometallic functions, for hydroxyl groups acyl functions. The protecting groups will be removed by standard techniques, for example hydrolysis, hydrogenolysis, etc. after the reactions step is complete.

Salt and chelate formation may be effected by conventional techniques, e.g. as described in the above mentioned patent publications.

The skeletons of the macrocyclic chelant groups or, more preferably, of the linker moiety, may be derivatised to enhance properties of the overall chelant, for example to include hydrophilic or lipophilic groups or biologically targetting groups or structures. Examples of macromolecules, biomolecules and macrostructures to which the polymeric chelant may be conjugated in this way include polymers (such as polylysine or polyethyleneglycol), dendrimers (such as first to sixth generation starburst dendrimers and in particular PAMAM dendrimers), polysaccharides, proteins, antibodies or fragments thereof (especially monoclonal antibodies or fragments such as Fab fragments), glycoproteins, proteoglycans, liposomes, aerogels, peptides, hormones, steroids, microorganisms, human or non-human cells or cell fragments, cell adhesion molecules (in particular nerve adhesion molecules such as are described in WO-A-92/04916), other biomolecules, etc). Generally such derivatisation will be achieved most conveniently by the introduction of alkyl- or aralkyl-carried functions, to which the macromolecule, biomolecule, etc. can be bound either directly or via a linker molecule, for example a bi- or polyfunctional acid, activated acid or oxirane.

In the case of conjugation to dendrimers, the dendrimer carriers can be produced by standard techniques, for example as desribed by Tomalia and by Nycomed Salutar in Angew Chem Int Ed Eng 29:138 (1990), WO-A-88/01178, WO-A-90/12050 and WO-A-93/06868 and the references cited therein.

Such macromolecular derivatives of the compounds of formula V and the metal chelates and salts thereof form a further aspect of the present invention.

The linkage of a compound of formula V to a macromolecule or backbone polymer may be effected by the methods of Nycomed Salutar (WO-A-90/12050) or by any of the conventional methods such as the carbodiimide method, the mixed anhydride procedure of Krejcarek et al. (see Biochemical and Biophysical Research Communications 77: 581 (1977)), the cyclic anhydride method of Hnatowich et al. (see Science 220: 613 (1983) and elsewhere), the backbone conjugation techniques of Meares et al. (see Anal. Biochem. 142: 68 (1984) and elsewhere) and Schering (see EP-A-331616 for example) and by the use of linker molecules as described for example by Nycomed Imaging in WO-A-89/06979 (U.S. Pat. No. 5,208,324).

Salt and chelate formation may be performed in a conventional manner. The chelating agents of formula V may be used in detoxification or in the formation of metal chelates, chelates which may be used for example in or as contrast agents for in vivo or in vitro magnetic resonance (MR), X-ray or ultrasound diagnostics (e.g. MR imaging and MR spectroscopy), or scintigraphy or in or as therapeutic agents for radiotherapy, and such uses of these metal chelates form a further aspect of the present invention.

Salts or chelate complexes of the compounds of the invention containing a heavy metal atom or ion are particularly useful in diagnostic imaging or therapy. Especially preferred are salts or complexes with metals of atomic numbers 20–32, 42–44, 49 and 57 to 83, especially Gd, Dy and Yb. For use as an MR-diagnostics contrast agent, the chelated metal species is particularly suitably a paramagnetic species, the metal conveniently being a transition metal or a lanthanide, preferably having an atomic number of 21–29, 42, 44 or 57–71. Metal chelates in which the metal species is Eu, Gd, Dy, Ho, Cr, Mn or Fe are especially preferred and $Gd^{3+}$, $Mn^{2+}$ and $Dy^{3+}$ are particularly preferred. Chelates of ions of these metals specifically listed above with chelants of formula V or their salts with physiologically tolerable counterions are particularly useful for the diagnostic imaging procedures mentioned herein and they and their use are deemed to fall within the scope of the invention and references to chelates of compounds of formula V herein are consequently to be taken to include such chelates.

The bislanthanide complexes of the compounds of formula V are especially preferred.

For diagnostic imaging purposes it is particularly important that the metal chelate complex be as stable as possible to prevent dissociation of the complex in the body.

In magnetic resonance imaging (MRI) it is frequently desirable to be able to target certain organs or tissues. In particular there is a need for improved hepatobiliary imaging MR contrast agents. Chelates of paramagnetic metals with compounds of formula V carrying one or more lipophilic groups are particularly suited for use as hepatobiliary MR contrast agents, since the presence of the lipophilic group will promote uptake by hepatocytes. By linking the lipophilic group to the molecule via a readily hydrolysable linking group such as an ester, the reabsorption after excretion to the intestine can be prevented.

The paramagnetic metal chelates of compounds of formula I, especially the chelates of high spin metal ions such as $Gd^{3+}$ and more especially $Dy^{3+}$, are particularly suitable for use as magnetic susceptibility (MS) contrast agents ($T_2$ or $T_2^*$ contrast agents) in MR imaging and other MR investigations. The use of paramagnetic metal monochelates is discussed by Villringer et al. in Mag. Reson. Med. 6:164–174 (1988) and by Kucharczyk et al. in U.S. Pat. No. 5,190,744 and WO-A-91/14186. Using the dimeric chelates of the present invention, smaller volumes of contrast medium can be administered to achieve the same MS effect thus allowing for more effective bolus dosing. Moreover, while for monochelates high susceptibility paramagnetic centres such as Dy(III) generally have to be used in MS studies, by using the dimeric chelates of the invention a wider range of paramagnetic metal centres, including in particular Gd(III) become useful.

For certain hepatobiliary imaging purposes it is desirable that the lipophilic contrast agent be precipitated as particles which can be taken up by Kupffer cells in the liver. In such cases it is preferred to use chelates of $Dy^{3+}$ with lipophilic compounds of formula V in conjunction with an imaging system utilising the magnetic susceptibility properties of the contrast agent; Kupffer cells in the liver are scarce and the contrast achievable using chelates with the gadolinium normally used in conventional MR imaging (i.e. as a $T_1$ relaxation agent) is generally insufficient. Such magnetic susceptibility agents form an important embodiment of the invention.

For use as contrast agents in MRI, the paramagnetic metal species is conveniently non-radioactive as radioactivity is a characteristic which is neither required nor desirable for MR-diagnostic contrast agents. For use as X-ray or ultrasound contrast agents, the chelated metal species is preferably a heavy metal species, for example a non-radioactive metal with an atomic number greater than 37, preferably greater than 50, e.g. $Dy^{3+}$.

For use in scintigraphy and radiotherapy, the chelated metal species must of course be radioactive and any conventional complexable radioactive metal isotope, such as $^{99m}Tc$, $^{67}Ga$ or $^{111}In$ for example, may be used. For radiotherapy, the chelating agent may be in the form of a metal chelate with for example $^{153}Sm$, $^{67}Cu$ or $^{90}Y$.

For use in detoxification of heavy metals, the chelating agent should be in salt form with a physiologically acceptable counterion, e.g. sodium, calcium, ammonium, zinc or meglumine, e.g. as the sodium salt of the chelate of the compound of formula V with zinc or calcium.

Where the metal chelate carries an overall charge, such as is the case with the prior art Gd DTPA, it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

The diagnostic and therapeutic agents of the present invention may be formulated with conventional pharmaceutical or veterinary formulation aids, for example stabilizers, antioxidants, osmolality adjusting agents, buffers, pH adjusting agents, etc. and may be in a form suitable for parenteral or enteral administration, for example injection or infusion or administration directly into a body cavity having an external escape duct, for example the gastrointestinal tract, the bladder or the uterus. Thus the agent of the present invention may be in a conventional pharmaceutical administration form such as a tablet, capsule, powder, solution, suspension, dispersion, syrup, suppository, etc; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g. 0.01 to 10 mole percent) of chelants (such as, for example, DTPA, DTPA-bisamide or non-complexed chelants of formula I) or calcium chelate complexes (as for example calcium DTPA, CaNaDTPA-bisamide, calcium salts or chelates of chelants of formula VII), or, optionally, additions (e.g. 1 to 50 mole percent) of calcium or sodium salts (for example, calcium chloride, calcium ascorbate, calcium gluconate or calcium lactate combined with metal chelate complexes of chelants of formula I and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavouring.

For MRI and for X-ray imaging of some portions of the body the most preferred mode for administering metal chelates as contrast agents is parenteral, e.g. intravenous administration. Parenterally administrable forms, e.g. intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Where the diagnostic or therapeutic agent comprises a chelate or salt of a toxic metal species, e.g. a heavy metal ion, it may be desirable to include within the formulation a slight excess of the chelating agent, e.g. as discussed by Schering in DE-A-3640708 (U.S. Pat. No. 5,098,692), or more preferably a slight excess of the calcium salt or such a chelating agent.

For MR-diagnostic examination, the diagnostic agent of the present invention, if in solution, suspension or dispersion form, will generally contain the metal chelate at concentration in the range 1 micromole to 1.5 mole per liter, preferably 0.1 to 700 mM. The diagnostic agent may however be supplied in a more concentrated form for dilution prior to administration. The diagnostic agent of the invention may conveniently be administered in amounts of from $10^{-3}$ to 3 mmol of the metal species per kilogram of body weight, e.g. about 1 mmol lanthanide (e.g. Dy or Gd)/kg bodyweight.

For X-ray examination, the dose of the contrast agent should generally be higher and for scintigraphic examination the dose should generally be lower than for MR examination. For radiotherapy and detoxification, conventional dosages may be used.

The disclosures of all of the documents mentioned herein are incorporated by reference.

The present invention will now be illustrated further by the following non-limiting Examples. All ratios and percentages given herein are by weight and all temperatures are in degrees Celsius unless otherwise indicated.

EXAMPLE 1

Synthesis of N,N'-Bis[1,4,7-tris-(carboxymethyl)-1, 4,7,10-tetraazacyclo-dodecan-1-methylcarbonyl] piperazine and the gadolinium complex thereof (a) 1,4,7,10-Tetraazacyclododecane (cyclen)

To a suspension of tetraaza-12-crown-4 tetrahydrochloride (66.6 g, 0.209 mol, Parish, Inc.) in chloroform (2 L), was bubbled $NH_3$ (g) through a gas dispersion tube for 1 hour. The solution was allowed to stir overnight and the white solid was filtered off and washed with $CHCl_3$ (4×100 mL). The combined filtrate was concentrated in vacuo to a white solid which was washed with diethyl ether (4×50 mL) and dried under vacuum at ambient temperature. A second crop of the free base was isolated from the ether washes to give a combined yield of 35.1 g (97.5%). $^1$H NMR ($CDCl_3$): $\delta$2.32 (s, 4 H), 2.70 (s, 16 H).

(b) 1,4,7-Tris-(tert-butoxy-carbonylmethyl)-1,4,7,10-tetraazacyclododecane-hydrobromide Cyclen (35.0 g, 0.203 mole) (Example 1(a)) was dissolved in N,N-dimethylacetamide (DMA, 600 mL) under nitrogen. Sodium acetate (50.0 g, 0.61 mol) was added at once and the mixture was allowed to stir for 0.5 hour. A solution of t-butylbromoacetate (118.9 g, 0.61 mol) in DMA (150 mL) was added dropwise from an addition funnel over a 7 hour period. The reaction mixture was allowed to stir for 19 days at ambient temperature under nitrogen during which time a white solid precipitated from solution. The white solid was then filtered off, washed with chilled DMA (75 mL) and ethyl acetate (100 mL), and dried under vacuum at 50° C. The filtrate was concentrated to approximately 500 mL and a second crop of white solid was collected in a similar manner. The combined solids (80.2 g+38.4 g) were taken up in $CHCl_3$ (600 mL) and washed with deionized $H_2O$ (4×100 mL). The organic layer was dried ($Na_2SO_4$), filtered, and concentrated to a light yellow oil. A white solid was obtained by addition of ethyl acetate to the oil. The solid was collected by filtration, washed with diethyl ether (2×75 mL), and dried under vacuum at 45° C. to give 67.4 g (55.7%) of the title monohydrobromide salt. Additional product can be recovered from the filtrates if desired. $^1$H NMR ($CDCl_3$): $\delta$1.42 (s, 27 H), 1.71 (s, 2 H), 2.86 (m, 12 H), 3.06 (br s, 4 H), 3.25 (s, 2 H), 3.34 (s, 4 H). Anal. Calcd (found) for $C_{26}H_{51}N_4O_6Br$: C, 52.43 (52.47); H, 8.63 (8.48); N, 9.40 (9.50); Br, 13.42 (12.92).

(c) Piperazine bis(bromoacetamide)

To a 1 L three-necked flask equipped with a magnetic stir bar, reflux condenser and addition funnel, was added bromo acetyl bromide (82.8 g, 0.41 mole) in $CHCl_3$ (170 mL). The addition funnel was charged with a solution of piperazine (0.2 mole, 17.2 g) and triethylamine (70 mL) in $CHCl_3$ (180 mL). The flask was chilled to −15° C. by means of a $CH_3CN$/liquid $N_2$ bath, and the amine was slowly added to the acid bromide. After the addition was complete the mixture was allowed to warm to ambient temperature and was stirred for 1 hour. The flask was then cooled to 0° C. and $H_2O$ (100 mL) was slowly added. The mixture was diluted with $CHCl_3$ (500 mL) and the layers were separated. The organic layer was extracted with $H_2O$ (5×50 mL), 0.05 N NaOH (5×50 mL) and $H_2O$ (200 mL), and dried ($Na_2SO_4$). The dark orange solution was filtered and concentrated to a beige solid. The material was purified by filtration through a bed of silica gel. The product eluted with 2–5% methanol/ $CH_2Cl_2$. After combining and concentrating the desired fractions, 15.0 g (49.2%) of a white solid was obtained. The title product was recrystallized from warm 2-propanol (400 mL) affording 9.95 g. $^1$H NMR ($CDCl_3$): $\delta$3.61 (dt, 6 H), 3.85 (s, 4 H).

(d) N,N'-Bis[1,4,7-tris-(tert-butoxycarbonylmethyl)-1,4,7,10-tetraazacyclododecan-10-yl-methylcarbonyl]-piperazine To a solution of the hydrobromide salt of Example 1(b) (10.0 g, 16.8 mmol) in $CHCl_3$ (20 mL) and THF (80 mL) was added 1,1,3,3-tetramethylguanidine (TMG, 1.93 g 16.8 mmol). A white solid was produced which was filtered off, washed with 20% $CHCl_3$/THF (100 mL) and identified as TMG.HBr. The filtrate was concentrated to a clear oil which was dissolved in N,N-dimethylformamide (DMF, 200 mL) and treated with the bisbromoacetamide of Example 1(c) (2.62 g, 8.0 mmol) and TMG (1.93 g). The light yellow solution was warmed to 60° C. and was allowed to stir for 16 hours under nitrogen. The reaction mixture was cooled to ambient temperature and the DMF was removed under vacuum. The residue was taken up in $CH_2Cl_2$ (300 mL) and was washed with 1 M $Na_2CO_3$ (3×60 mL). The combined aqueous layer was back-extracted with $CH_2Cl_2$ (50 mL). The combined $CH_2Cl_2$ layers were extracted with 1 M HCl (2×80 mL) followed by deionized $H_2O$ (2×50 mL). The combined HCl and $H_2O$ layers were washed with $CH_2Cl_2$ (50 mL). The aqueous layer was combined with $CH_2Cl_2$ (250 mL) in an Erlenmeyer flask, and the pH was adjusted to 9–10 with anhydrous $Na_2CO_3$. The neutralized mixture was transferred to a separating funnel and the layers were separated. The aqueous layer was extracted with $CH_2Cl_2$ (2×100 mL), and all of the basic $CH_2Cl_2$ layers were combined and washed with $H_2O$ (2×70 mL). The organic layer was dried ($Na_2SO_4$), filtered, and concentrated to give 12.3 g of an off-white solid. The solid was triturated with ethyl acetate (50 mL) collected by filtration, washed with ethyl acetate (2×20 mL), diethyl ether (30 mL), and dried under vacuum to give 8.40 g (76%) of a white solid. This material analyzed as the title dimer containing two NaX molecules (where X=Cl or Br). $^1$H NMR ($CD_3OD$): $\delta$1.39 (s, 54 H), 1.9–3.5 (br m, 56 H). $^{13}$C NMR ($CD_3OD$): $\delta$174.5, 174.4, 172.2, 82.8, 82.6, 79.5, 56.7, 56.3, 54.0 (br), 49.0 (br), 45.2, 44.9, 42.9, 42.6, 28.5, 28.4. MS (FAB): m/e 1218 ($MNa^+$). Anal: Calculated (found) for $C_{60}H_{110}N_{10}O_{14}Na_2Cl_2.4H_2O$: C, 52.04 (52.14); H, 8.59 (8.68); N, 10.12 (10.07); Na, 3.32 (3.44); Cl, 5.12 (5.16).

(e) N,N'-Bis[1,4,7-tris-(carboxymethyl)-1,4,7,10-tetraazacyclododecan-10-yl-methylcarbonyl]-piperazine A solution of the dimer of Example 1(d) (10.0 g, 7.2 mol) in $CH_2Cl_2$ (120 mL) and trifluoroacetic acid (TFA, 80 mL) was allowed to stir at ambient temperature for 1 hour. The volatiles were removed by rotary evaporation to give a thick brown oil. The residue was redissolved in $CH_2Cl_2$ and trifluoroacetic acid as above for 1 hour. The process had to be repeated seven times to completely remove all of the t-butyl groups. After the final treatment with TFA, the crude product was concentrated, dissolved in $H_2O$ (100 mL) and reconcentrated by rotary evaporation. The $H_2O$ chase was repeated several times. The product was precipitated as a white solid by dissolving the crude mixture in $H_2O$ (20 mL), warming the solution to 50° C. and adding 2-propanol (150 mL) slowly. The solid was collected by filtration and washed with 2-propanol (2×50 mL) and acetone (2×30 mL). A second crop of product was collected from the filtrate and isolated in a similar fashion. The combined solids were dried under vacuum to give 7.48 g of material that contained traces of sodium and TFA. A portion of the solid, (5.24 g) was dissolved in $H_2O$ (10 mL) and the pH was adjusted to 10.9 with 2 N NaOH. The solution was loaded onto a column containing Bio-Rad AG1-X8 (acetate form) and the column was washed with $H_2O$ (2 L). The product was then eluted with 0.1 N acetic acid. After combining desired fractions and concentrating, the product was precipitated by dissolving in $H_2O$ (50–60° C.) and slowly adding 2:1 acetone/ethanol (60 mL). The solid was collected, washed with 2:1 acetone/ethanol (60 mL), and dried in vacuo to give 3.31 g (50%) of the title product. $^1$H NMR (NaOD, $D_2O$): $\delta$2.20 (br s, 16 H), 2.46 (br s, 16 H), 2.88 (s, 12 H), 3.26 (d, 4 H), 3.40 (s, 8 H). $^{13}$C NMR (NaOD, $D_2O$): $\delta$180.7, 180.6, 172.4, 59.3, 59.2, 54.9, 54.6, 51.2 (br), 44.6, 44.5, 41.9, 41.8. MS (FAB): m/e 859.5 ($MH^+$). Anal: calculated (found) for $C_{36}H_{62}N_{10}O_{14}.4.5H_2O$: C, 46.00 (46.00); H, 7.61 (7.45); N, 14.90 (15.01).

(f) Bisgadolinium complex of N,N'-Bis[1,4,7-tris-(carboxymethyl)-1,4,7,10-tetraazacyclododecan-10-yl-methylcarbonyl]-piperazine To a suspension of the dimeric chelant of Example 1(e) (5.65 g, 6.0 mmol) in deionized $H_2O$ (120 mL) was added gadolinium acetate (4.73 g). A clear slightly yellow solution formed within minutes. The mixture was stirred at ambient temperature for 3 hours and was then concentrated by rotary evaporation (50° C.) to drive off acetic acid. The residue was redissolved in $H_2O$ (150 mL) and the solution was warmed to 40° C. No gadolinium was detected after 2 hours by a xylenol orange test. Gadolinium acetate was added in 12.2 mg (0.5 mol %) increments until a positive test for free gadolinium was observed. The solution was then treated with ligand to adjust the titer to $\leq$0.1 mol % excess ligand. The complex was precipitated by dissolving in $H_2O$ (40° C.) and adding a 2:1 acetone/ethanol solution. The solid was collected by filtration, washed with 2:1 acetone/ethanol (2×25 mL) and dried under vacuum at 35° C. to give 6.4 g (80%) of the title product. MS (FAB): m/e 1168 ($MH^+$). Anal: Calculated (found) for $C_{36}H_{56}N_{10}O_{14}Gd_2.8.75H_2O$: C, 32.64 (32.48); H, 5.58 (5.16); N, 10.57 (10.42); Gd, 23.73 (23.31).

EXAMPLE 2

Synthesis of N,N'-bis[1,4,7-tris-(carboxymethyl)-1,4,7,10-tetraazacyclododecan-10-yl-methylcarbonyl]-N,N'-dimethylethylenediamine and the gadolinium complex thereof (a) N,N'-Dimethylethylenediamine bis(bromoacetamide)

To a 1 L three-necked flask equipped with a magnetic stir bar, reflux condenser and addition funnel, was added bromoacetyl bromide (46.95 g, 232.6 mmole) and $CHCl_3$ (100 mL). The addition funnel was charged with a solution of N,N'-dimethylethylenediamine (10.0 g, 113.4 mmol) and triethylamine (39.5 mL) in $CHCl_3$ (100 mL). The flask was chilled to −15° C. by means of an ethylene glycol/$CO_2$ bath, and the amine was slowly added to the acid bromide. After the addition was complete, the mixture was allowed to warm to ambient temperature and stirred for 1 hour. The flask was then cooled to 0° C. and $H_2O$ (50 mL) was slowly added. The mixture was diluted with $CHCl_3$ (250 mL) and the layers were separated. The organic layer was extracted with $H_2O$ (3×50 mL), 0.05 N NaOH (3×50 mL), and $H_2O$ (2×50 mL), and was dried ($Na_2SO_4$). The solution was filtered and concentrated. The material was methanol purified by filtration through a bed of silica gel. The product eluted with 2–5% methanol/$CH_2Cl_2$. After combining and concentrating the desired fractions, 14.95 g (39.9%) of a beige solid was obtained. The title product was recrystallized from warm 2-propanol affording 11.94 g.

$^1$H NMR ($CDCl_3$): $\delta$[2.99 (s), 3.11 (s), 3.13 (s); 6 H], [3.53 (s), 3.57 (s); 4 H], 3.81 (s), 3.84 (s), 3.91 (s); 4 H].

(b) N,N'-Bis[1,4,7-tris-(tert-butoxycarbonylmethyl)1,4,7,10-tetraazacyclododecan-10-yl-methylcarbonyl]-N,N'-dimethylethylenediamine To a solution of the hydrobromide salt of Example 1(b) (8.0 g, 13.4 mmol) in $CHCl_3$ (20 mL) and THF (80 mL) was added 1,1,3,3-tetramethylguanidine (TMG, 1.547 g, 13.4 mmol)). A white solid was produced which was filtered off, washed with 20% $CHCl_3$/THF (100 mL) and identified as TMG.HBr. The filtrate was concentrated to a clear oil which was dissolved in N,N-dimethylformamide (DMF, 200 mL) and treated with the bis(bromoacetamide) of Example 2(a) (2.21 g, 6.7 mmol) and TMG (1.547 g). The light yellow solution was warmed to 60° C. and was allowed to stir for 16 hours under nitrogen. The reaction mixture was cooled to ambient temperature and the DMF was removed under vacuum. The residue was taken up in $CHCl_3$ (200 mL) and washed with 1 M $Na_2CO_3$ (3×40 mL). The combined aqueous layer was back-extracted with $CHCl_3$ (50 mL). The combined $CHCl_3$ layers were extracted with 0.8 M HCl (2×50 mL) followed by deionized $H_2O$ (2×50 mL). The combined HCl and $H_2O$ layers were washed with $CHCl_3$ (50 mL). The aqueous layer was combined with $CHCl_3$ (200 mL) in an Erlenmeyer flask and the pH was adjusted to between 9.5 with $Na_2CO_3$. The neutralized mixture was transferred to a separating funnel and the layers were separated. The aqueous layer was extracted with $CHCl_3$ (2×100 mL), and the basic $CHCl_3$ layers were combined and washed with $H_2O$ (2×50 mL). The organic layer was dried over anhydrous $Na_2SO_4$, filtered and concentrated to give 7.50 g (93%) of the title product as a yellow oil. $^1H$ NMR ($CDCl_3$): δ1.24 (s, 54 H), 1.90–3.39 (br m, 67 H). $^{13}C$ NMR ($CDCl_3$): δ27.7, 27.8, 34.9. 45.7, 48.3 (br), 52.0 (br), 55.4, 55.6, 56.3, 81.4, 81.6, 81.6, 81.7, 81.8, 171.5, 172.6, 172.7.

(c) N,N'-Bis[1,4,7-tris-(carboxymethyl)-1,4,7,10 tetraazacyclododecan-10-yl-methylcarbonyl]-N,N-dimethylethylenediamine A solution of the dimer of Example 2(b) (7.50 g) in $CH_2Cl_2$ (100 mL) and trifluoroacetic acid (TFA, 60 mL) was allowed to stir at ambient temperature for 1 hour. The volatiles were removed by rotary evaporation to give a thick brown oil. The residue was redissolved in $CH_2Cl_2$ (20 mL) and trifluoroacetic acid (15 mL) as above for 1 hour. The process was repeated seven times to completely remove all of the t-butyl groups. After the final treatment with TFA, the crude product was concentrated, dissolved in $H_2O$ (100 mL) and reconcentrated by rotary evaporation. The $H_2O$ chase was repeated several times. The product was purified by ion-exchange chromatography (Bio Rad AG1-X8, acetate form) using 0.1 N acetic acid to elute the product. Desired fractions were combined and concentrated to give 2.36 g (37%) of the title product as an off white solid after lyophilization. $^1H$ NMR (NaOD, $D_2O$): δ2.0–3.7 (br, m). $^{13}C$ NMR (NaOD, $D_2O$): δ34.5, 35.4 (br), 43.7, 45.6, 47.2, 47.2, 48.9, 49.6, 50.0, 51.6 (br), 52.5, 55.1, 56.0, 57.3, 59.1, 63.3, 173.4 (br), 179.2, 180.5, 181.4. MS (FAB): m/e 861 ($MH^+$), 883 ($MNa^+$), 917 $(M+NaCl-H)^+$], 973 [$(M+2NaCl-2H)^+$].

(d) Bisgadolinium complex of N,N'-Bis[1,4,7-tris(carboxymethyl)-1,4,7,10-tetraazacyclododecan-10-yl-methylcarbonyl]-N,N-dimethyl-ethylenediamine To a solution of the dimeric chelant of Example 2(c) (1.88 g, 2.0 mmol) in deionized $H_2O$ (40 mL) was added gadolinium acetate (1.53 g). The light yellow solution was stirred at 40° C. for 1 hour and was then concentrated by rotary evaporation (50° C.) to drive off acetic acid. The residue was redissolved in $H_2O$ (100 mL) and the solution was warmed to 40° C. The reaction was allowed to stir overnight at ambient temperature. Gadolinium acetate was added in 0.01 mmol increments until a positive test for free gadolinium was observed. The solution was then treated with ligand to adjust the titer to 0.1 mol % excess ligand. The solution was concentrated to dryness and was triturated with 2:1 diethylether/$CHCl_3$ to give the title product as a beige solid (2.57 g, 98%)

EXAMPLE 3

Synthesis of N,N'-Bis[1,4,7-tris-(carboxymethyl)-1,4,7,10-tetraazacyclododecan-10-yl-methylcarbonyl] tetrahydroquinoxaline and the gadolinium complex thereof (a) Tetrahydroquinoxaline bis(chloroacetamide)

To a 1 L three-necked round bottomed flask equipped with a magnetic stir bar, reflux condenser and addition funnel, was added chloroacetyl chloride (9.6 mL, 0.120 mol) and $CHCl_3$ (100 mL). The addition funnel was charged with a solution of tetrahydroquinoxaline (8.0 g, 0.0596 mol) and triethylamine (20.8 mL) in $CHCl_3$ (100 mL). The flask was chilled to 0° C., and the amine was slowly added to the acid chloride. After the addition was complete, the mixture was allowed to warm to ambient temperature and stir for 1 hour. The flask was then cooled to 0° C. and $H_2O$ (50 mL) was slowly added. The mixture was diluted with $CHCl_3$ (250 mL) and the layers were separated. The organic layer was washed with $H_2O$ (50 mL), 0.05 N NaOH (2×50 mL), $H_2O$ (50 mL), 1 N HCl (3× 50 mL) and $H_2O$ (2×50 mL), and was dried over anhydrous $Na_2SO_4$. The solution was filtered and concentrated to a brown solid. The solid was collected by filtration, washed with 2-propanol (2×30 mL) and diethyl-ether (2×40 mL) and dried to yield the title product (4.41 g, 51.5%). $^1H$ NMR (DMSO-d6): δ3.89 (s, 4 H), 4.01 (s, 4 H), 7.25 (s, 2 H), 7.65 (br s, 2 H).

(b) N,N'-Bis[1,4,7-tris-(tert-butoxycarbonylmethyl)-1,4,7,10-tetraazacyclododecan-10-yl-methylcarbonyl] tetrahydroquinoxaline To a solution of the hydrobromide salt of Example 1(b) (8.0 g, 13.4 mmol) in $CHCl_3$ (20 mL) and THF (80 mL) was added 1,1,3,3-tetramethylguanidine (TMG, 1.547 g, 13.4 mmol)). A white solid was produced which was filtered off, washed with 20% $CHCl_3$/THF (100 mL) and identified as TMG.HBr. The filtrate was concentrated to a clear oil which was dissolved in N,N-dimethylformamide (DMF, 250 mL) and treated with bis(chloroacetamide) of Example 3(a) (1.928 g, 6.72 mmol) and TMG (1.547 g). The light yellow solution was warmed to 60° C. and was allowed to stir for approximately 16 hours under nitrogen. The reaction mixture was cooled to ambient temperature and the DMF was removed under vacuum. The residue was taken up in $CHCl_3$ (200 mL) and was washed with 1 M $Na_2CO_3$ (3×40 mL). The combined aqueous layer was back-extracted with $CHCl_3$ (50 mL). The combined $CHCl_3$ layers were extracted with 1 M HCl (2×50 mL) followed by deionized $H_2O$ (2×50 mL). The combined HCl and $H_2O$ layers were washed with $CHCl_3$ (2×50 mL). The aqueous layer was combined with $CHCl_3$ (250 mL) in an Erlenmeyer flask, and the pH was adjusted to 9.5 ($Na_2CO_4$). The neutralized mixture was transferred to a separating funnel and the layers were separated. The aqueous layer was extracted with $CHCl_3$ (2×50 mL), and all $CHCl_3$ layers were combined and washed with brine (2×40 mL). The organic layer was dried ($Na_2SO_4$), filtered, and concentrated to give 10.60 g of a yellow oil. The title product was purified further by passing through a bed of silica gel and eluting the product with 10% methanol/CHCl$_3$ to give 7.06 g (84.6%). $^1$H NMR (CDCl$_3$): δ1.30 (s), 1.38 (s), 1.41 (s), 2.0–3.7 (br m), 7.28 (s).

(c) N,N'-Bis[1,4,7-tris-(carboxymethyl)-1,4,7,10-tetraazacyclododecan-10yl-methylcarbonyl]tetrahyquinoxaline A solution of the dimer of Example 3(b) (7.06 g) in CH$_2$Cl$_2$ (70 mL) and trifluoroacetic acid (TEA, 60 mL) was allowed to stir at ambient temperature for 1 hour. The volatiles were removed by rotary evaporation to give a thick brown oil. The residue was redissolved in CH$_2$Cl$_2$ (70 mL) and trifluoroacetic acid (60 mL) as above for 1 hour. The process was repeated nine times to completely remove all of the t-butyl groups. After the final treatment with TFA, the crude product was concentrated, dissolved in H$_2$O (100 mL), and reconcentrated by rotary evaporation. The H$_2$O chase was repeated several times. The product was purified by ion-exchange chromatography column (Bic Rad AG1-X8, acetate form) using 0.1 N acetic acid to elute the product. Desired fractions were combined and concentrated to give 3.26 g of an off white solid after lyophilization The solid was triturated with ethanol (50 mL), collected by filtration, washed with diethyl ether and dried to yield the title product (3.18 g, 48%). $^1$H NMR (NaOD, D$_2$O): δ[2.88 (br s), 3.19 (br s), 3.43 (s), 3.53–3.68 (m); 56 H], 7.07 (m, 3 H), 7.59 (br s, 1 H).

(d) Bisgadolinium complex of N,N'-bis[1,4,7-tris(carboxymethyl)-1,4,7,10-tetraazacyclododecan-10-yl-methylcarbonyl]-tetrahyquinoxaline To a solution of the dimeric chelant of Example 3(c) (2.50 g, 2.53 mmol) in 100 mL deionized H$_2$O (100 mL) was added gadolinium acetate (1.9827 g, 96% of theroretical). The clear solution was stirred at 40° C. for 1 hour and was then concentrated by rotary evaporation (50° C.) to drive off acetic acid. The residue was redissolved in H$_2$O (100 mL) and the solution was warmed to 40° C. and the reaction allowed to stir overnight at ambient temperature. Gadolinium acetate was added in 0.5 mol % increments until a positive test for gadolinium was observed. The solution was then treated with ligand to adjust the titer to 0.5 mol % excess ligand. The solution was lyophlized to give 3.28 g of the title product as an off-white solid. Mass spectrum (FAB): m/e 1217 (MH$^+$).

EXAMPLE 4

Synthesis of N,N'-Bis[1,4,7-tris-(carboxymethyl)-1,4,7,10-tetraazacyclododecan-10-yl-methylcarbonyl]ethylenediamine and the gadolinium complex thereof (a) Ethylenediamine bis(chloroacetamide)

To a solution of ethylenediamine (3.0 g, 0.05 mol) in CHCl$_3$ (50 mL) cooled to –15° C. was added chloroacetyl chloride (7.96 mL, 9.10 mol) in CHCl$_3$ (40 mL) dropwise. A white precipitate formed and the reaction mixture was stirred overnight at ambient temperature. After 16 hours the reaction mixture was filtered and the white solid was washed with CHCl$_3$ (30 mL) followed by water (100 mL). The CHCl$_3$ layer was washed with water (2×25 mL), dried (Na$_2$SO$_4$) and filtered. After being dried under vacuum, the white solid was recrystallized from ethanol and filtered hot to give a clear filtrate from which the product crystallized upon standing. The solid was collected by filtration and washed with isopropyl alcohol (20 mL). The mother liquor from the recrystallization and the CHCl$_3$ layer were combined and concentrated yielding a white solid which was recrystallized from ethanol and then washed with isopropyl alcohol. The title product (4.9 g, 46%) was obtained as a white solid. $^1$H NMR (CDCl$_3$) δ7.05 (br, 2 H), ⁻4.04 (s, 4 H), 3.49 (s, 4 H). $^{13}$C NMR (DMSO-d$_6$) δ166.2, 42.7, 38.5.

(b) N,N'-Bis[1,4,7-tris-(tert-butoxycarbonylmethyl)-1,4,7,10-tetraazacyclododecan-10-yl-methylcarbonyl-ethylenediamine The hydrobromide salt of Example 1(b) (4.7 g, 7.9 mmol) was dissolved in 20% CHCl$_3$/THF (50 mL). To this solution was added TMG (0.99 mL, 7.9 mmol) with the solution quickly becoming cloudy as TMG.HBr precipitated. After stirring for 15 minutes, the solution was filtered and the filtrate concentrated to a yellow oil. The oil was taken up in THF (80 mL) and transfered to a three necked round bottom flask. The flask was then charged with NaI (590 mg, 3.9 mmol), TMG (0.99 mL, 7.9 mmol), and finally the bischloroacetamide of Example 4(a) (837 mg, 3.93 mmol). The reaction mixture was placed under N$_2$ and heated to 68° C. After 16 hours, the reaction mixture was filtered and the filtrate concentrated to a gummy solid. The residue was taken up in CH$_2$Cl$_2$ and washed with 1.0 N Na$_2$CO$_3$ (3×50 mL). The aqueous phase was back extracted with CH$_2$Cl$_2$. The organic portions were combined and extracted with 1 M HCl (1×80 mL). The aqueous phase was then washed with CH$_2$Cl$_2$ and the pH of the aqueous phase was adjusted to 9 with Na$_2$CO$_3$. The aqueous layer was then extracted with CH$_2$Cl$_2$ (1×200 mL, 2×100 mL) and the CH$_2$Cl$_2$ layer washed with water (2×75 mL), dried (MgSO$_4$), and filtered. Concentration and drying under vacuum yielded 3.6 grams (79%) of the title compound as a pale yellow solid. $^1$H NMR (CDCl$_3$) δ3.34–2.00 (br band, 57 H), 1.44 (br s, 54 H).

(c) N,N'-Bis[1,4,7-tris-(carboxymethyl)-1,4,7,10-tetraazacyclododecan-10-yl-methylcarbonyl]-ethylenediamine The ethylenediamine dimer of Example 4(b) (6.7 g; 5.7 mmol) was dissolved in CH$_2$Cl$_2$ (40 mL) and a 1:1 solution of TFA/CH$_2$Cl$_2$ (20 mL) was added. The resulting mixture was stirred for one hour and then concentrated. This procedure was repeated eight times to complete the deprotection. After the final deprotection, the solution was concentrated and chased with water (3×25 mL) to yield a 6.2 grams of a brownish solid. The solid was dissolved in water (15 mL), the pH was adjusted to 10.9 with 3 N LiOH, and the solution was loaded onto AG1-X8 ion exchange resin. (acetate form). The column bed was washed with water (1 L), and the diner eluted from the column with 0.1 N acetic acid with the desired fractions being combined and concentrated yielding 2.5 g (51%) of the title product as a pale yellow solid. $^1$H NMR (D$_2$O) δ3.62–2.89 (br band).

(d) Bisgadolinium complex of N,N'-bis[1,4,7-tris-(carboxymethyl)-1,4,7,10-tetraazacyclododecan-10-yl-methylcarbonyl]ethylenediamine The dimeric chelant of Example 4(c) (2.12 g, 2.32 mmol) was dissolved in water (50 mL) and gadolinium acetate (1.81 g, 2.25 mmol) was added. The mixture was allowed to stir at ambient temperature for 1.5 hours, the solution was concentrated, and the residue was taken up in water (50 mL). After another 1.5 hours, the solution gave a positive xylenol orange test, therefore the solution was concentrated and chased with water (1×20 mL). The residue was taken up in water (50 mL) and allowed to stir overnight at ambient temperature. After stirring for 16 hours, the solution was chased with water to remove the acetic acid formed. Additional ligand was added in 21 mg (0.07 mmol) portions until the xylenol orange test gave a positive (purple) color. A final portion of 21 mg of ligand was added and the solution was stirred for two hours at 40° C. A xylenol orange test was performed and gave a negative result. The solution was then concentrated to give a pale yellow solid. The solid was dissolved in warm water (15 mL) to which was added a 2:1 acetone/ethanol solution (85 mL) from which a white solid precipitated. The solid was collected by filtration and washed with 2:1 acetone/ethanol solution (200 mL) followed by acetone (30 mL) and dried in a vacuum oven (35° C.) for 3.5 hours to yield 2.4 g of the title product as a white solid. MS (FAB): m/e 1143.2 (MH$^+$). Anal: Calculated for $C_{34}H_{54}Gd_2N_{10}O_{14}$.3.4$H_2O$: C,29.53; H,5.89; Gd,22.74; N,10.13. Found C,29.47; H,5.59; Gd,22.54; N,9.81.

EXAMPLE 5

Synthesis of N,N'-bis[1,4,7-tris-(carboxymethyl)-1, 4,7,10-tetraazacyclododecan-10-yl-methylcarbonyl] homopiperazine and the gadolinium complex thereof (a) Homopiperazine bis(chloroacetamide)

Homopiperazine (10 g; 100 mmol) was dissolved in chloroform (150 mL) and triethylamine (28 mL; 200 mmol) was added to the mixture. The solution was cooled to −30° C. under nitrogen and chloroacetyl chloride (17 mL, 213 mmol) was added over a period of 1 hour. The solution was stirred at −30° C. for 1 hour, at 0° C. for 2 hour and at ambient temperature overnight. The solution was washed with water (4×50 mL), dried over anhydrous MgSO$_4$, filtered and concentrated. The oily residue was purified by column chromatography on silica gel (5% methanol in chloroform) to yield the title product as an oil which solidified on prolonged standing (10.3 g; 41%). $^1$H NMR (CDCl$_3$): 4.04 (m, 4 H), 3.62 (m, 8 H), and 1.94 (m, 2 H).

(b) N,N'-Bis[1,4,7-tris-(tert-butoxycarbonylmethyl)-1,4, 7,10-tetraazacyclododecan-10-yl-methylcarbonyl] homopiperazine A solution of the bis(chloroacetamide) of Example 5(a) (1.7 g, 6.72 mmol), DO3A-tri-t-butyl ester (8 g, 13.43 mmol) and tetramethylguanidine (2.6 mL, 20.75 mmol) in acetonitrile (300 mL) was heated at 60° C. for 25 hours under nitrogen. The solvent was removed under reduced pressure and the residue redissolved in chloroform (60 mL). The solution was washed with 1 M sodium carbonate (2×50 mL) and water (2×50 mL) and extracted with 1 M HCl (4×50 mL) followed by water (2×50 mL). The aqueous extracts were combined and basified with solid sodium carbonate. The crude product that separated as an oil was extracted with chloroform (3×100 mL), dried over anhydrous magnesium sulfate, filtered, and concentrated to yield the crude title product as a yellow solid (9.77 g). $^1$H NMR (CDCl$_3$): 3.44–2.45 (m, 56 H), 1.84 (s, 2 H), 1.42 (s, 18 H), 1.40 (s, 36 H).

(c) N,N'-Bis[1,4,7-tris-(carboxymethyl)-1,4,7,10-tetraazacyclododecan-10-yl-methylcarbonyl] homopiperazine A solution of the crude t-butyl ester of Example 5(b) (9.77 g) in CH$_2$Cl$_2$ (30 mL) was treated with trifluoroacetic acid (30 mL) and the mixture stirred at ambient temperature for 1 hour. The solution was concentrated and the process-repeated seven times. The oily residue (10.5 g) obtained after the final deprotection was dissolved in acetone (30 mL) and was precipitated with chloroform. Filtration and drying under vacuum yielded a yellow solid (8.33 g). The solid was dissolved in water (20 mL) and the pH of the solution was adjusted to 11.0 with 3.0 N LiOH. The solution was loaded onto an AG1-X8 ion exchange column (acetate form) and the column bed was washed with water (1 L). The desired dimer was eluted with 0.1 N acetic acid with the desired fractions being combined and and concentrated. Lyophilzation of the product yielded 3.8 g (54%) of the title product as a yellow solid. $^1$H NMR (D$_2$O) δ3.63–2.74 (br band, 56 H), 1.6 (br s, 2 H)

(d) Bisgadolinium complex of N,N'-bis[1,4,7-tris-(carboxymethyl)-1,4,7,10-tetraazacyclododecan-10-yl-methylcarbonyl]homopiperazine To the dimeric chelant of Example 5(c) (3.11 g, 3.26 mmol) dissolved in water (60 mL) was added gadolinium acetate (2.52 g, 6.30 mmol). The solution was warmed to 40° C. for one hour and then concentrated to remove the acetic acid formed. Water (60 mL) was again added, the solution was stirred for one hour, and the process to remove the acetic acid repeated. The solid was then taken up in water (60 mL) and stirred overnight at ambient temperature. The solution gave a weakly positive xylenol orange test, therefore ligand (31 mg, 0.07 mmol) was added. After 1.5 hours at 40° C. the reaction mixture gave a negative xylenol orange test. The solution was concentrated and then dissolved in ethanol. Acetone was added and the precipitated complex collected by filtration. The solid was taken up in acetone and stirred for 1 hour and then collected by filtration. The solid was dried in a vacuum oven (35° C.) for two hours to give 3.2 g (76%) of the title product as a fine white powder. MS (FAB): m/e 1183.3 (MH$^+$). Anal: Calculated for $C_{37}H_{58}Gd_2N_{10}O_{14}$.12.3 $H_2O$.0.72 acetone: C,32.55; H,6.06; Gd,21.77; N,9.69. Found C,32.92; H,5.69; Gd,21.47; N,9.91.

EXAMPLE 6

Synthesis of N,N'-bis[1,4,7-tris-(carboxymethyl)-1, 4,7,10-tetraazacyclododecan-10-yl-methylcarbonyl]-2,2'-(ethylenedioxy)diethylamine and the gadolinium complex thereof (a) 2,2'-(Ethylenedioxy)diethylamine bis (chloroacetamide)

To a solution of 2,2'(ethylenedioxy)diethylamine (10.0 g, 0.0675 mol) in CH$_2$Cl$_2$ (190 mL) was added Na$_2$CO$_3$ (14.2 g, 0.135 mol). The resulting mixture was chilled in an ice-bath and placed under a stream of N$_2$ to which was added chloroacetyl chloride (10.7 mL, 0.135 mol) in CH$_2$Cl$_2$ dropwise over a period of 25 minutes. Upon completion of addition, the ice bath was removed and the mixture was stirred at ambient temperature for two hours. The reaction mixture was then filtered and the filtrate was washed with water (150 mL), saturated NaHCO$_3$ (150 mL), and finally water (150 mL). The organic phase was dried (over Mg$_2$SO$_4$), filtered, and concentrated to yield a yellow oil which solidified when placed under vacuum. The solid was triturated with a 1:1 mixture of ethyl acetate/hexane (150 mL). A white solid was collected by filtration and dried in a vacuum oven (50° C.) for 6 hours yielding 6.9 g (34%) of the title product. $^1$H NMR (CDCl$_3$) δ6.97 (br s, 2 H), 4.03 (s, 4 H), 3.60 (s, 4 H), 3.56 (distorted t, 4 H), 3.50 (t, 4 H); $^{13}$C NMR (CDCl) δ165.9, 70.1, 69.1 42.4, 39.3.

(b) N,N'-Bis[1,4,7-tris-(tert-butoxycarbonylmethyl)-1,4, 7,10-tetraazacyclododecan-10-yl-methylcarbonyl]-2,2'-(ethylenedioxy)diethylamine The hydrobromide salt of Example 1(b) (19.8 g, 33.2 mmol) was dissolved in 20% CHCl$_3$/THF (250 mL). To this solution was added TMG (4.16 mL, 33.2 mmol) and the solution quickly became cloudy as TMG.HBr precipitated. After stirring for 20 minutes, the solution was filtered with the filtrate being concentrated to a thick yellow oil. The residue was taken up in THF (100 mL) and transferred to a 1 L flask which was then charged with NaI (2.48 g, 16.6 mmol), TMG (4.16 ml, 33.2 mmol), and finally the bis (chloroacetamide) of Example 6(a) (5.0 g, 16.6 mmol). Additional THF (150 mL) was added, the system was placed under a stream of $N_2$, and the reaction mixture was heated to 65° C. After four days, the reaction mixture was filtered and the filtrate concentrated to a reddish solid. The solid was taken up in $CH_2Cl_2$ (110 mL) and washed with water (3×100 mL). The organic portion was dried ($MgSO_4$), filtered and concentrated to yield 22.14 g (114%) of the title product as a tacky yellow solid which was not analyzed for salts. $^1H$ NMR ($CDCl_3$) δ3.39–2.06 (br band, 62 H), 1.25 (br s, 54 H).

(c) N,N'-Bis[1,4,7-tris-(carboxymethyl)-1,4,7,10-tetraazacyclododecan-10yl-methylcarbonyl]-2,2'-(ethylenedioxy)diethylamine The crude dimer of Example 6(b) (22.0 g, 18.7 mmol) was dissolved in $CH_2Cl_2$ (25 mL). To this solution was added a mixture of TFA (25 mL) and $CH_2Cl_2$ (10 mL). After stirring for 2 hours at ambient temperature, the reaction was concentrated. This procedure was repeated seven times to complete the deprotection. After the final deprotection, the solution was concentrated and chased with water (3×40 mL). The reddish semi-solid was then dissolved in water (30 mL) and the pH adjusted to 2.3 with 3.0 N $NH_4OH$. The solution was loaded onto an AG50-X8 ion-exchange resin ($H^+$ form) and the column bed washed with water (1.8 L). The dimer was eluted from the column with 0.5 N $NH_4OH$ with the desired fractions being combined and concentrated to yield 9.8 g (57%) of the title product as a yellow solid. $^1H$ NMR ($D_2O$) δ3.61–2.92 (br band). MS (FAB): m/e 921.4 ($MH^+$).

(d) Bisgadolinium complex of N,N'-bis[1,4,7-tris-(carboxymethyl)-1,4,7,10-tetraazacyclododecan-10-yl-methylcarbonyl]-2,2'-(ethylenedioxy)diethylamine To a solution of the DO3A dimer of Example 6(c) (5.90 g, 5.94 mmol) in water (50 mL) was added gadolinium acetate (3.61 g, 8.91 mmol) and the reaction mixture was warmed to 40° C. for 1.5 hours at which time the xylenol orange test was negative. Gadolinium acetate (240 mg, 0.594 mmol) was added in increments until a positive (purple) xylenol orange was achieved. Ligand was then added to achieve a negative xylenol orange test. The solution was reduced in volume and lyophilized yielding 7.58 g of crude complex. The crude complex was purified by HPLC employing a reverse phase C18 column using 2% methanol/water as the mobile phase. MS (FAB): m/e 1231.0 ($MH^+$) Anal: Calculated for $C_{38}H_{62}Gd_2N_{10}O_{16}$·7.65$H_2O$: C,33.38; H,5.70; Gd,23.00; N,10.24. Found C,33.48; H,5.79; Gd,22.75; N,10.50.

EXAMPLE 7

Synthesis of N,N'-bis[1,4,7-tris-(carboxymethyl)-1, 4,7,10-tetraazacyclododecan-10-yl-methylcarbonyl]-N,N'-bis(2,3-dihydrozypropyl)-ethylenediamine and the gadolinium complex thereof (a) 1,2,5,6-Di-isopropylidene-D-mannitol To a solution of (411 g, 3.01 mol) of $ZnCl_2$ in 1.5 L of acetone cooled to 0° C. was added (250 g, 1.37 mol) of D-mannitol and the mixture stirred at ambient temperature for 5 hours. The solid was filtered off and the filtrate poured into a solution of diethyl ether (1.8 L) and potassium carbonate (470 g, 3.4 mol) producing vigorous bubbling. The solution was stirred for 1 hour. A white precipitate was filtered off and the filtrate was dried ($K_2CO_3$), and concentrated leaving a white solid which was recrystallized from n-butyl ether to give 160 g (50%) of the title product as white needles. $^1H$ NMR ($CDCl_3$) δ4.2 (m, 4 H), 4.0 (t, 2 H), 3.7 (d, 2 H), 2.7 (s, 2 H), 1.4 (d, 12 H).

(b) Isopropylidene-glyceraldehyde

The mannitol derivative of Example 7(a) (81 g, 0.311 mol) was suspended in $CH_2Cl_2$ (1.1 L) and saturated $NaHCO_3$ (40 mL) and stirred at ambient temperature. Sodium periodate (100 g, 0.47 mol) was added in four portions over 20 minutes and the solution was stirred vigorously at 0° C. for 3 hours. The solvent was decanted off and the remaining solid was stirred in $CH_2Cl_2$ and then filtered to remove the excess solid. The two organic portions were combined and concentrated in vacuo. The resulting oil was distilled at reduced pressure to give the title product as a clear, viscous oil. Yield (59 g, 75%). $^1H$ NMR ($CDCl_3$) δ4.3 (t, 1 H), 3.9 (m, 2 H), 1.4 (d, 6 H).

(c) N,N'-Bis(2,3-dihydroxypropyl)ethylenediamine bisacetonide

Ethylene diamine (13.2 g, 0.22 mol) was dissolved in methanol (150 mL) and the solution was adjusted with a 1:1 HCl/methanol mixture to pH 7. The solution was cooled with an ice bath and isopropylidene-glyceraldehyde of Example 7(b) (59 g, 0.45 mol) was added followed by portionwise addition of $NaCNBH_3$ (28.3 g, 0.45 mol). The reaction mixture was stirred at 25° C. under $N_2$ for 72 hours. The pH of the solution was then lowered to 3 with HCl/methanol and the solvent was stripped off in vacuo. The solid was taken up in $H_2O$ and extracted with diethyl ether (3×200 mL). The pH of the aqueous phase was raised to 11 and extracted again with diethyl ether (4×200 mL). The ether washes were combined, dried ($MgSO_4$) and concentrated to a yellow oil. The title product was isolated by flash chromatography. (5% methanol/$CHCl_3$). Yield (37 g, 58%). $^1H$ NMR ($CDCl_3$) δ4.1 (m, 4 H), 3.3 (m, 2 H), 2.6 (m, 8 H), 1.4 (d, 12 H).

(d) N,N'-Bis(2,3-dihydroxypropyl)ethylenediamine bisacetonide bischloroacetamide The compound of Example 7(c) (37 g, 0.13 mol) and triethylamine (25.96 g, 0.25 mol) were combined in $CH_2Cl_2$ (300 mL). Chloroacetyl chloride (28.9 g, 0.25 mol) was added dropwise at 0° C. under $N_2$. A color change was observed along with a white precipitate as the reaction mixture was allowed to return to ambient temperature. After 24 hours, $H_2O$ (150 mL) was added, the organic layer was separated, washed with water (3×100 mL), dried ($MgSO_4$) and concentrated to a dark viscous oil. The title product (23 g, 41%) was isolated by flash chromatography, 10% methanol/$CHCl_3$. MS (FAB): m/e 442 ($MH^+$).

(e) N,N'-Bis[1,4,7-tris-(tert-butoxycarbonylmethyl)-1,4, 7,10-tetraazacyclododecan-10-yl-methylcarbonyl]N,N'-bis (2,3-dihydroxypropyl)ethylenediamine bisacetonide The hydrobromide salt of Example 1(b) (12 g, 0.02 mol) and the compound of Example 7(d) (4.5 g, 0.01 mol) were dissolved in $CH_3CN$ (300 mL) and tetramethylguanidine (7.6 mL, 0.61 mol). The reaction mixture was heated to 60° C. and stirred under $N_2$ for 6 days. The solvent was stripped off and the resulting dark oil taken up in $CHCl_3$ and extracted with water (3×100 mL), dried ($MgSO_4$) and concentrated to give (12 g, 80%) of the title product MS(FAB): m/e 1398 ($MH^+$).

(f) N,N'-Bis[1,4,7-tris-(carboxymethyl)-1,4,7,10-tetraazacyclododecan-10-yl-methylcarbonyl]N,N'-bis(2,3-dihydroxypropyl)ethylenediamine The dimer of Example 7(e) was dissolved in $CHCl_3$ (175 mL) and trifluoroacetic acid (175 mL) was added dropwise.

The reaction mixture was allowed to stir for 1 hour at ambient temperature under $N_2$ and then concentrated in vacuo to a dark oil. The acid treatment was repeated ten times to remove all t-butyl groups and the acetonides. The solvent was stripped off and the title product purified via preparative HPLC. (Supelco activated C18 reverse-phase column, 3% methanol mobile phase). Yield (9 g, 85%); MS (FAB): m/e 982 ($MH^+$).

(g) Gadolinium complex of N,N'-bis[1,4,7-tris-(carboxymethyl)-1,4,7,10-tetraazacyclododecan-10-yl-methylcarbonyl]-N,N'-bis(2,3-dihydroxypropyl) ethylenediamine The dimeric chelant of Example 7(f) (10 g, 10.2 mmol) was dissolved in $H_2O$ (175 mL). Gadolinium triacetate (5.45 g, 0.016 mol, 80% of the theoretical stoichiometric amount) was added and the pH was adjusted to 7 using $NH_4OH$. The reaction mixture was stirred at 50° C. for 2 hours. Additional Gadolinium triacetate was added in 5 mol % increments until a xylenol orange test for gadolinium was positive. The reaction was stirred for an additional 24 hours and the xylenol orange test repeated, giving a positive result. Purification of the title product was achieved by preparative HPLC (supelco activated C18 reverse-phase column, 100% $H_2O$ mobile phase) to yield (500 mg, 5%) MS (FAB): m/e 1290 ($MH^+$) Anal. calculated for $C_{40}H_{66}Gd_2N_{10}O_{18}$·3 $H_2O$: C, 35.76; H, 5.4; Gd, 23.36; N, 10.43; found C, 35.3; H, 5.59; Gd, 23.17; N, 10.9.

EXAMPLE 8

Synthesis of N,N'-bis[1,4,7-tris-(carboxymethyl)-1,4,7,10-tetraazacyclododecan-10-yl-methylcarbonyl]-N,N'-bis(2-hydroxyethyl)ethylenediamine and the gadolinium complex thereof (a) bis(BOC)-bis(2-hydroxyethyl)ethylene diamine N,N'-bis(hydroxyethyl)ethylene diamine (2 g; 13.5 mmol) was dissolved in methanol and the solution was treated with di-t-butyl dicarbonate (6.0 g; 27.5 mmol). The solution was stirred at ambient temperature for 9 hours under nitrogen and concentrated. The residue was washed with petroleum ether and dried under vacuum to obtain the title product as a colorless solid (4.48 g; 95.3%). $^1H$ NMR ($CDCl_3$): δ1.42 (s, 18H), 3.44–3.35 (m, 8H), 3.44 (s), 3.7 (m, 4H), 4.89 (br s, 2H).

(b) Bis(BOC)-bis(2-benzyloxyethyl)ethylenediamine

An 80% mineral oil suspension of sodium hydride (0.75 g; 25 mmol) was washed with tetrahydrofuran under a blanket of nitrogen and re-suspended in tetrahydrofuran (25 mL). Benzyl bromide (20 mL; 169 mmol) and the diamine of Example 8(a) (4.37 g; 12.54 mmol) were added in succession. Following a vigorous initial reaction, the suspension was stirred overnight at ambient temperature under nitrogen. The solution was concentrated under vacuum and the excess benzyl bromide was distilled off under vacuum at 40° C. and the residue containing approximately 10% benzyl bromide was dried under vacuum to yield the title product as a yellow solid (7.18 g, 108%). $^1H$ NMR ($CDCl_3$): δ1.39 (s, 9H), 1.42 (s, 9H), 3.38–3.66 (m, 10H), 4.49 (s, 4H), 7.29 (m, 10H)

(c) Bis(2-benzyloxyethyl)ethylenediamine

The diamine of Example 8(b) (7.18 g) was dissolved in $CH_2Cl_2$ (40 mL) and cooled to 0° C. Trifluoroacetic acid (35 mL) was added and the solution was stirred at ambient temperature for 2 hours. After concentration, the title product was washed with petroleum ether and dried under vacuum. Yield 7.2 g (93%). $^1H$ NMR ($CDCl_3$): δ7.27 (m, 10H), 4.46 (s, 4H), 3.65 (t, 4H), 3.44 (s, 4H), 3.11 (t, 4H).

(d) Bis(chloroacetyl)-bis(2-benzyloxyethyl) ethylenediamine

A solution of the compound of Example 8(c) (6.81 g; 20.75 mmol) and triethylamine (5.0 mL, 41.5 mmol) in $CH_2Cl_2$ (250 mL) was cooled to 0° C. under nitrogen and chloroacetyl chloride (3.3 mL, 41.5 mmol) was added dropwise with stirring. The solution was stirred at ambient temperature for 24 hours and washed with water (7×20 mL), dried ($MgSO_4$), and concentrated. The crude title product was purified by column chromatography on silica gel (ether eluent) to give 2.94 g (29%). $^1H$ NMR ($CDCl_3$): δ7.28 (m, 10 H), 4.44 (m, 4 H), 4.21 (d, 4 H), 3.65–3.35 (s); 3.35 (m, 12 H).

(e) N,N'-Bis[1,4,7-tris-(tert-butoxycarbonylmethyl)-1,4,7,10-tetraazacyclododecan-19-yl-methylcarbonyl)bis(2-benzyloxyethyl)ethylenediamine A solution of the diamine of Example 8(d) (2.94 g, 6.1 mmol), the hydrobromide salt of Example 1(b) (7.27 g, 12.2 mmol), sodium iodide (0.9 g, 6.1 mmol), and tetramethylguanidine (2.3 mL, 18.3 mmol) in acetonitrile (130 mL) was heated at 60° C. under nitrogen for 19 hours. The solvent was removed under vacuum and the residue was redissolved in $CH_2Cl_2$ (150 mL), washed with water (100 mL), 1 M $Na_2CO_3$ (2×100 mL) and water (100 mL). The organic layer was extracted with 1 M HCl (4×100 mL) and water (100 mL). The combined aqueous layer was basified with solid $Na_2CO_3$ and extracted with $CH_2Cl_2$ (4×100 mL). The organic layer was dried ($Na_2SO_4$) and concentrated. The crude title product (11 g, 62%) was obtained as a brown solid. $^1H$ NMR ($CDCl_3$): δ7.28 (m, 10 H), 4.45 (m, 8 H), 3.89–2.58 (m, 60 H), 1.45 (s, 18 H), 1.32 (s, 32 H).

(f) N,N'-Bis[1,4,7-tris-(carboxymethyl)-1,4,7,10-tetraazacyclododecan-10-yl-methylcarbonyl]bis (benzyloxyethyl)ethylene diamine The crude dimer of Example 8(e) (11 g) was dissolved in $CH_2Cl_2$ (50 mL) and treated with trifluoroacetic acid (40 mL). The mixture was stirred at ambient temperature for 1 hour and concentrated. This process was repeated seven times. After the final deprotection the product was chased with $CH_2Cl_2$ (3×15 mL) and water (3×15 mL) and purified by ion-exchange chromatography on BioRad AG1 X-8 resin (100–200 mesh, acetate form), eluting with 0.1 M acetic acid. Further purification was effected by precipitation of the product from methanol by the addition of acetone, when the title product separated as a yellow solid (4.08 g; 47%). $^1H$ NMR($D_2O$): δ7.15 (s, 10 H), 4.30 (m, 4 H), 3.60 (s), 3.60–2.87 (m, 60 H).

(g) N,N'-Bis[1,4,7-tris-(carboxymethyl)-1,4,7,10-tetraazacyclododecan-10-yl-methylcarbonyl]bis(2-hydroxyethyl)ethylenediamine The dimer of Example 8(f) (4.05 g; 3.68 mmol) was dissolved in a mixture of water (25 mL) and glacial acetic acid (15 mL) and treated with Pearlman's catalyst (2 g) and the mixture was hydrogenated in a Parr apparatus at 52 psi until the hydrogen uptake ceased. The solution was then filtered and concentrated. The residue was dissolved in methanol (50 mL) and precipitated with acetone addition (100 mL). This process was repeated again and the title product, a pale yellow solid was dried under vacuum. Yield: 3.07 g (88.6%). $^1H$ NMR ($D_2O$): δ3.59–2.93 (m). $^{13}C$ NMR ($D_2O$): δ177.05; 171.74; 171.4; 169.87; 169.52; 58.52; 58.35; 56.14; 55.45; 55.28; 55.04; 52.26; 52.36; 50.97; 50.38; 49.81; 48.85; 48.59; 47.84; 44.33; 43.68; 42.97; 38.68; 37.96; 29.85.

(h) Bisgadolinium complex of N,N'-bis[1,4,7-tris-(carboxymethyl)-1,4,7,10-tetraazacyclododecan-10-yl-methylcarbonyl]bis(2-hydroxyethyl)-ethylenediamine The dimeric chelant of Example 8(g) (3.0 g, 3.26 mmol) was dissolved in water (30 mL) and gadolinium acetate (2.38 g, 5.86 mmol) was added. The solution was stirred at ambient temperature for 2 hours and at 40° C. for 3 hours. It was then concentrated, chased with water and redissolved in water. The solution gave a positive xylenol orange test. Addition of the ligand (in 1 weight % increments) followed by heating at 40° C. for 1 hour was continued until the solution gave a negative xylenol orange test. The solution was then concentrated and chased with water (2×20 mL). Further purification by precipitation from methanol/acetone solvent system (×6) and passage through BioRad AG1-X8 resin (acetate form) yielded the title product as a yellow solid (3.13 g, 78%). MS (FAB): m/e: 1230 (MH$^+$). Final purification for toxicity studies was effected by semi-preparative HPLC on a C18 column. Elemental analysis; calculated for $C_{38}H_{62}Gd_2N_{10}O_{16}.13.1\ H_2O$: C 31.15%, H 6.07%, Gd 21.46%, N 9.56%; found: C 31.27%, H 5.61%, Gd 21.0% N 9.56%.

EXAMPLE 9

Synthesis of N,N'-bis[1,4,7-tris-(carboxymethyl)-1, 4,7,10-tetraazacyclododecan-10-yl-methylcarbonyl]-1-(N-methylglucaminecarbonyl)-ethylenediamine and bisgadolinium complex thereof (a) N-BOC-N-methylglucamine N-methylglucamine (4.0 g; 20.49 mmol) and di-t-butyl dicarbonate (4.48 g; 20.51 mmol) were dissolved in methanol (40 mL) and the solution was stirred under nitrogen for 24 hours. Concentration and washing with petroleum ether yielded the title product as a colorless solid (6.48 g, 100%). $^1$H NMR (D$_2$O): δ3.59–3.38 (m, 6 H), 3.1 (s, 2 H), 2.67 (br, 3 H), 1.21 (s, 9 H).

(b) N-BOC-N-methyl-pentakis-(O-benzyl)glucamine

An 80% suspension of sodium hydride (1.5 g, 50 mmol) was washed with tetrahydrofuran (20 mL) under nitrogen. Benzyl bromide (17.8 mL, 150 mmol) and tetrahydrofuran (30 mL) were added followed by N-BOC-N-methylglucamine (Example 9(a), 2.95 g, 10 mmol). The mixture was stirred at ambient temperature under nitrogen overnight. The reaction was quenched by the gradual addition of water (30 mL) with stirring. The organic layer was separated and the aqueous layer extracted with CH$_2$Cl$_2$ (2×30 mL). The combined organic extract was washed with water, dried (MgSO$_4$) and concentrated to obtain a yellow oil from which the excess benzyl bromide was distilled off under vacuum at a bath temperature of 100° C. The crude title product was obtained as a sticky yellow solid (7 g; 94%). $^1$H NMR (CDCl$_3$): δ7.38 (m, 25 H), 4.79–4.44 (m, 10 H), 4.04–3.76 (m, 6 H), 3.49 (m, 2 H), 2.96 (s), 2.78 (d, 3 H), 1.48–1.44 (d, 9 H). $^{13}$C NMR (CDCl$_3$): 155.72; 138.53 (m); 127.68 (m); 79.0–76.49 (m); 73.93–69.60 (m); 49.96; 35.94; 28.41.

(c) N-Methyl-pentakis(O-benzyl)glucamine

The crude glucamine of Example 9(b) (7.02 g, 9.43 mmol) was dissolved in CH$_2$Cl$_2$ (25 mL) and the solution was cooled in an ice bath. Trifluoroacetic acid (40 mL) was added and the mixture was stirred at ambient temperature for 2 hours. The solution was concentrated and the deprotection process was repeated again. The solution was chased with CH$_2$Cl$_2$ (2×15 mL), washed with saturated NaHCO$_3$ (30 mL), water (30 mL), dried (Na$_2$SO$_4$), and concentrated to yield the title product as a brown oil which was purified by chromatography on silica gel using 5% methanol in chloroform as the eluent. Yield: 5.55 g (91%). $^1$H NMR (CDCl$_3$): δ7.33 (m, 25 H), 4.8–4.41 (m, 10 H), 4.06–3.61 (m, 6 H) 3.03–2.71 (m, 2 H), 2.41 (s, 3 H). $^{13}$C NMR (CDCl$_3$): δ137.97 (m); 128.25; 78.85–69.55 (m); 50.41; 39.94.

(d) N,N'-Bis(BOC)-2,3-diaminopropionic acid

A suspension of diaminopropionic acid hydrochloride (5.13 g, 36.5 mmol) in a mixture of ethanol (70 mL) and methanol (20 mL) was treated with triethylamine (10.2 mL, 73 mol), diisopropylethylamine (5 ml) and di-t-butyldicarbonate (16.72 g, 76.6 mmol). The mixture was stirred at ambient temperature overnight and refluxed for 7 hours under nitrogen. The solution was filtered and concentrated. The residue was washed with petroleum ether (3×20 mL), treated with chloroform (150 mL) and the mixture cooled to 0° C. 1 M H$_2$SO$_4$ (150 mL) was added and the mixture was stirred at 0° C. for 15 minutes. The aqueous layer was removed and extracted with chloroform (2×30 mL). The combined organic layers were washed with water, dried (Na$_2$SO$_4$) and concentrated to obtain the title product as a colorless solid (9.57 g; 86.3%). $^1$H NMR (CDCl$_3$): δ7.34 (br, 1 H), 6.25–5.19 (br, 2 H), 4.3 (br, 1 H), 3.52 (m, 2 H), 1.42 (s, 18 H). $^{13}$C NMR (CDCl$_3$): δ173.32; 54.69; 42.22; 28.29.

(e) N,N'-Bis(BOC)-(N-methyl-pentakis-O-benzyl-glucaminocarbonyl)-ethylenediamine A mixture of the propionic acid of Example 9(d) (2.24 g, 7.37 mmol), dicyclohexylcarbodiiimide (1.52 g, 7.37 mmol), the glucamine of Example 9(c) (4.76 mg, 7.37 mmol) and dimethylaminopyridine (0.09 mg, 0.74 mmol) in CH$_2$Cl$_2$ (50 mL) was stirred at ambient temperature under nitrogen overnight. The solution was filtered, washed with water, dried (MgSO$_4$) and concentrated to give a brown oil. Purification by column chromatography on silica gel (chloroform eluent) yielded the title product (6.19 g; 90%) $^1$H NMR (CDCl$_3$): δ7.32 (m, 25 H), 4.81–4.65 (m, 10 H), 4.04–3.75 (m, 4 H), 1.45 (d, 18 H). $^{13}$C NMR (CDCl$_3$): δ170.17, 169.92, 155.8, 155.2, 138.21, 127.76, 79.46–76.49 (m), 74.30–69.21 (m), 50.78–48.65 (n), 42.59, 36.31, 28.15, 28.1, 25.46, 24.81.

(f) N-methyl-pentakis(O-benzyl)glucamine-carbonylethylenediamine

The ethylenediamine of Example 9(e) (5 g) was dissolved in CH$_2$Cl$_2$ (60 mL) and the solution was cooled to 0° C. Trifluoroacetic acid (60 mL) was added and the solution was stirred at ambient temperature for 2 hours. The solution was concentrated and the process was repeated again. After concentration the residue was chased with CH$_2$Cl$_2$ (3×15 mL), dissolved in CHCl$_3$, and washed with saturated NaHCO$_3$ (2×30 mL) and water and dried (MgSO$_4$). The title product was obtained as a brown oil after concentration (4.72 g). $^1$H NMR (CDCl$_3$): δ7.3 (m, 25 H), 4.76–4.25 (m, 11 H), 3.96–3.41 (m, 10 H), 2.94–2.52 (m, 3 H). $^{13}$C NMR (CDCl$_3$): δ138.62, 127.7, 78.89–76.5 (m), 74.63–69.55 (m), 53.62–46.0 (m), 39.62–24.90. MS (FAB): m/e: 732.6 (MH$^+$).

(g) N-Methyl-pentakis(O-benzyl)glucaminecarbonyl-ethylenediamine-bis(chloroacetamide)

The ethylenediamine of Example 9(f) (3.9 g, 5.33 mmol) and triethylamine (1.5 mL, 10.7 mmol) were dissolved in chloroform (50 mL) and the solution was cooled to 0° C. under nitrogen. Chloroacetyl chloride (1.2 g, 10.6 mmol) was added slowly. After the addition was complete the solution was warmed to ambient temperature and stirred overnight. The solution was washed with water (3×20 mL), dried (MgSO$_4$) and concentrated. The residue was chromatographed on silica gel, eluting with methanol/chloroform solvent mixture (0–5%) to yield the title product 3.82 g (81%). $^1$H NMR (CDCl$_3$): δ7.30 (m, 25 H), 4.78–4.40 (m, 10 H), 4.30 (m, 1 H), 4.01–3.19 (m, 14 H), 2.94–2.51 (m, 3 H). $^{13}$C NMR (CDCl$_3$): δ168.85–165.55 (m), 137.98–137.5 (m), 127.86–126.74 (m), 78.29–75.55 (m), 74.09–71.38 (m), 68.94–68.72 (m), 49.08–48.64 (m), 42.14–40.99 (m), 36.5; 35.8, 33.76–33.1, 25.07, 24.41. MS (FAB): m/e 884.4 (MH$^+$).

(b) N,N'-Bis[1,4,7-tris-(tert-butoxycarbonyl-methyl)-1,4,7,10-tetraazacyclododecan-10-yl-methyl-carbonyl]-N-methyl-pentakis(O-benzy)glucamine-carbonyl-ethylenediamine The hydrobromide salt of Example 1(b) (5.12 g, 8.6 mmol) and the bis(chloroacetamide) of Example 9(g) (3.8 g, 4.3 mmol) were dissolved in CH$_3$CN (100 mL) and tetramethylguanidine (1.62 mL, 12.9 mmol) was added. The solution was heated at 60° C. under nitrogen for 25 hours. After concentration, the residue was taken up in chloroform and washed with water and dried (MgSO$_4$). Following concentration, the crude title product was obtained as a viscous yellow material (9.08 g). $^1$H NMR (CDCl$_3$): δ7.22 (m, 25 H), 4.70–4.32 (m, 11 H), 4.00–3.67 (m, 6 H), 3.38–2.49 (m, 55 H), 1.39–1.35 (m, 54 H). $^{13}$C NMR (CDCl$_3$): δ174.27–169.56 (m), 138.5–136.6 (m), 132.49–127.11 (m), 81.06–80.16 (m), 78.62–76.49 (m), 73.62–69.37 (m), 57.62–47.28 (m), 36.9; 27.97. MS (FAB): m/e 1842.1 (MH$^+$).

(i) N,N'-Bis[1,4,7-tris-(carboxymethyl)-1,4,7,10-tetraazacyclododecan-10-yl-methylcarbonyl]-N-methyl-pentakis(O-benzy)glucamine-carbonylethylenediamine The dimer of Example 9(h) (7.9 g, 4.29 mmol) was dissolved in dichloromethane (80 mL) and cooled to 0° C. Trifluoroacetic acid (80 mL) was added and the solution was stirred at ambient temperature for 1 hour. The solution was concentrated and the process was repeated nine times. After the final deprotection, the solution was concentrated and chased with CH$_2$Cl$_2$ (4×20 mL) and water (4×20 mL). Drying under vacuum yielded the crude title product (10.9 g). $^1$H NMR (D$_2$O): δ6.53 (br, 25 H), 4.08–2.37 (m, 72 H). $^{13}$C NMR (D$_2$O): δ126.33, 52.33, 51.05, 50.13, 47.27, 45.68, 40.27. MS (FAB): m/e 1504.5 (MH$^+$).

(j) N,N'-Bis[1,4,7-tris-(carboxymethyl)-1,4,7,10-tetraazacyclododecan-10-yl-methylcarbonyl]-1-(N-methyl-glucaminecarbonyl)-ethylenediamine A solution of the dimer of Example 9(i) (0.86 g, 0.57 mol) in water (20 mL) was treated with glacial acetic acid (5 mL) and Pearlman's catalyst (0.5 g). The mixture was hydrogenated in a Parr hydrogenation apparatus with hydrogen gas at a pressure of 53 psi until no further uptake of hydrogen was observed. The solution was filtered, concentrated and chased with water. The residue was purified by ion exchange chromagraphy using BioRad AG1-X8 resin (100–200 mesh, acetate form) using acetic acid as the eluent (0.05–0.2 M) to give 0.42 g (70%) of the title product as a pale yellow solid. $^1$H NMR (D$_2$O): δ3.8–2.66 (m). $^{13}$C NMR (D$_2$O): δ175.17, 179.46, 172.17–170.77, 72.22–70.61, 63.31, 56.87–48.77, 40.59–35.18. MS (FAB): m/e 1054.6 (MH$^+$).

(k) Synthesis of Bisgadolinium complex of N,N'-bis[1,4,7-tris-(carboxy-methyl)-1,4,7,10-tetraazacyclododecan-10-yl-methylcarbonyl]-1-(N-methylglucamine-carbonyl) ethylenediamine To a solution of the dimeric chelant of Example 9(j) (0.94 g, 0.89 mmol) in water (25 mL) was added gadolinium acetate (0.47 g) and the solution was stirred at 40° C.

overnight. It was concentrated and the solution was repeatedly chased with water until the pH was to 5.2. The xylenol orange test for free gadolinium was negative. Further quantities of gadolinium acetate were added in 1 weight % increments and the solution heated at 40° C. for 1 hour until the reaction mixture showed a postive xylenol orange test for gadolinium. The solution was filtered, concentrated, and chased with water. The crude title product was subjected to purification by semi-preparative HPLC on a C18 column using 2% methanol in water, followed by precipitation from a methanol solution with acetone to give 0.78 g (52%). MS (FAB): m/e 1364.3 (MH$^+$).

EXAMPLE 10

Synthesis of bis[1,4,7-tris-(carboxymethyl)-1,4,7,10-tetraazacyclododecan-10-yl]-2-oxo-3-aza-pentane and the gadolinium and dysprosium complexes thereof (a) 3-Aza-4-oxo-1,5-dibromopentane Bromoethylamine hydrobromide (6.15 g, 30 mmol) was suspended in chloroform (40 mL) and treated with diisopropylethylamine (5.2 mL, 60 mmol). The solution was cooled in a dry ice acetone bath and a solution of bromoacetyl bromide (2.6 mL, 30 mmol) in chloroform (10 mL) was added dropwise under nitrogen. After the addition was complete, the solution was warmed to ambient temperature and stirred overnight. The solution was washed successively with water (2×30 mL), 1 M acetic acid (2×30 mL), water (30 mL), 1 M NaOH (2×30 mL) and water (2×30 mL). Drying over anhydrous Na$_2$SO$_4$ followed by concentration yielded the crude product as a colorless solid (4.94 g; 66%). Recrystallization from chloroform yielded the pure title product (1.33 g, 18.1%). $^1$H NMR (CDCl$_3$): δ6.84 (br, 1 H), 3.91 (s, 2 H), 3.72 (q, 2 H), 3.5 (t, 2 H). $^{13}$C NMR (CDCl$_3$): δ166.08, 41.54, 31.11, 28.67.

(b) Bis[1,4,7-tris-(tert-butoxycarbonylmethyl)-1,4,7,10-tetraazacyclododecan-10-yl]-2-oxo-3-aza-pentane 3-Aza-4-oxo-1,5-dibromopentane (Example 10(a), 1.28 g, 5.22 mmol), the hydrobromide salt of Example 1(b) (6.22 g, 10.44 mmol) and tetramethylguanidine (2 mL, 15.66 mmol) were dissolved in acetonitrile (125 mL) and the solution was heated at 60° C. for 48 hours under nitrogen. The solution was concentrated, the residue was dissolved in chloroform and washed with water. It was dried over anhydrous Na$_2$SO$_4$ and concentrated to yield a brown oil. Petroleum ether extraction followed by concentration of the extract yielded the crude title product (6.26 g). $^1$H NMR (CDCl$_3$): 8.8 (br, 1 H), 3.46–2.38 (m, 50 H), 1.28 (s, 54 H). $^{13}$C NMR (CDCl$_3$): δ172.2–169.84, 80.47, 61.83–47.37, 27.94, 27.9. MS (FAB): m/e 1112.9 (MH$^+$).

(c) Bis[1,4,7-tris-(carboxymethyl)-1,4,7,10-tetraazacyclododecan-10-yl]-2-oxo-3-aza-pentane To a solution of the dimer of Example 10(b) (6.25 g) in CH$_2$Cl$_2$ (60 mL) cooled in an ice bath, is added trifluoroacetic acid (60 mL) and the mixture stirred at ambient temperature for 1 hour. The solution is concentrated and the process is repeated nine times. After the final deprotection, the solution is concentrated and chased with CH$_2$Cl$_2$ (3×20 mL) and water (3×20 mL). The residue is passed through BioRad AG1 X-8 ion exchange resin (100–200 mesh, acetate form) and the product eluted with aqueous acetic acid (0.05–0.1 M acetic acid).

(d) Bisgadolinium complex of bis[1,4,7-tris-(carboxymethyl)-1,4,7,10-tetraazacyclododecan-10-yl]-2-oxo-3-aza-pentane The dimeric chelant of Example 10(c) is dissolved in water and gadolinium acetate is added. The solution is stirred at 40° C. for 2 hours. The pH of the solution is raised from 3 to 5 by adding 0.1 M ammonium hydroxide followed by chasing with water. Addition of gadolinium acetate in 1 wt. % increments and heating at 40° C. is continued until a positive xylenol orange test is observed. The solution is then filtered and concentrated. The residue is chased with water and dried under vacuum to obtain the title product.

(e) Bis dysprosium complex of bis[1,4,7-tris-(carboxymethyl)-1,4,7,10-tetraazacyclododecan-10-yl]-2-oxo-3-aza-pentane The dysprosium complex is prepared analogously to Example 10(d) using the dimeric chelant of Example 10(c) and a soluble dysprosium(III) salt.

EXAMPLE 11

1,8-Bis[4,7,10-tris(carboxymethyl)-1,4,7,10-tetraazacyclododec-1-yl]-2,7-dioxo-3,6-diazaoctane (EthylDOTA Dimer)

(a) 1,8-Bis[4,7,10-tris(2-ethoxy-2-oxoethyl)-1,4,7,10-tetraazacyclododec-1-yl]-2,7-dioxo-3,6-diazaoctane (EthylDOTA-hexaethylester Dimer)

To a stirred solution of K$^+$DOTA-Triethylester (23.8 g, 0.0453 mol) in 500 mL of anhydrous tetrahydrofuran is added dicyclohexylcarbodiimide (9.33 g, 0.0453 mol) and 1-hydroxybenzotriazole (6.07 g, 0.0453 mol). The suspension is stirred for 15 minutes at ambient temperature and ethylenediamine (1.51 ml, 0.0226 mol) is added. After stirring an additional 24 hours at ambient temperature, the suspension is filtered and the solvents are evaporated. The residue is dissolved in 800 mL of ethyl acetate and is washed with 800 mL of saturated, aqueous sodium bicarbonate. Flash chromatography of the residue affords 18.0 g of EthylDOTA-hexaethylester dimer.

(b) 1,8-Bis[4,7,10-tris(carboxymethyl)-1,4,7,10-tetraazacyclododec-1-yl]-2,7-dioxo-3,6-diazaoctane (EthylDOTA Dimer)

To a stirred solution of EthylDOTA-hexaethylester dimer (15.0 g, 0.0163 mol) in 100 mL of tetrahydrofuran is added 200 mL of a 1 N sodium hydroxide solution. After stirring at ambient temperature for 4 hours, sufficient Bio-Rad AG50-X8 resin is added to the solution to adjust the pH to 2.2. The suspension is filtered and the filtrate is evaporated and lyophilized to provide the title product (11.5 g).

EXAMPLE 12

Experimental Results

Gadolinium complexes of a series of dimeric substituted tetraazacyclododecane macrocycles (Table 1) have been synthesized. Their physicochemical properties were studied to evaluate their utility as extracellular fluid MRI contrast agents. The results are presented here.

Experimental

The DO3A bis(amide) dimer ligands 1–12 shown in Table 1 were prepared by the coupling reaction of DO3A-tri-t-butyl ester with bis(chloroacetamides) of the appropriate diamines, followed by the deprotection of the t-butyl ester groups. The gadolinium complexes were prepared by the reaction of the ligands with Gd(OAc)$_3$. Relaxivities were measured in water and in serum (in selected cases) at 40° C. and 20 MHz. Viscosities and osmolalities were measured at concentrations listed in Table 2.

Conclusion

The favourable physicochemical profiles of the dimeric gadolinium chelates presented here, which include relaxivity, viscosity and osmolality suggest their potential use as new extracellular fluid MRI contrast agents.

| Compound No. | D* |
|---|---|
| 1 | NHCH$_2$CH$_2$NH |
| 2 | N(CH$_3$)CH$_2$CH$_2$N(CH$_3$) |
| 3 | N(CH$_2$CH$_2$OH)CH$_2$CH$_2$N(CH$_2$CH$_2$OH) |
| 4 | N(CH$_2$CHOHCH$_2$OH)CH$_2$CH$_2$N(CH$_2$CHOHCH$_2$OH) |
| 5 | NHCH(CON(CH$_3$)CH$_2$(CHOH)$_4$CH$_2$OH)CH$_2$NH |
| 6 | piperazine |
| 7 | homopiperazine |
| 8 | NHCH$_2$CH$_2$OCH$_2$CH$_2$NH |
| 9 | NHCH$_2$CH$_2$OCH$_2$CH$_2$OCH$_2$CH$_2$NH |
| 10 | N(CH$_3$)CH$_2$CH$_2$OCH$_2$CH$_2$OCH$_2$CH$_2$N(CH$_3$) |

-continued

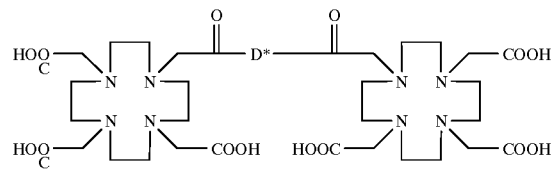

| Compound No. | D* |
|---|---|
| 11 | $NH(CH_2CH_2O)_3CH_2CH_2NH$ |
| 12 | 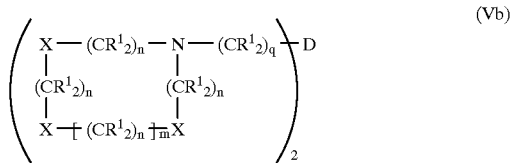 |

TABLE 2

Physicochemical properties of complexes

| Complex | Relaxivity[a] ($mM^{-1} sec^{-1} Gd^{-1}$) | | Osmolality[b] (mmol/kg) | Viscosity[c] (cPs) | |
|---|---|---|---|---|---|
| | $r_1$ | $r_2$ | | 25° C. | 37° C. |
| 1 | 4.9 | 5.6 | 425 (250) | 2.4 | 1.7 |
| 2 | 5.6 | 5.5 | 323 (200) | 2.0 | 1.4 |
| 3 | 5.2 | 4.9 | 555 (200) | 2.1 | 1.5 |
| 4 | 5.5 | 6.2 | 345 (275) | .[d] | .[d] |
| 5 | 6.1 | 6.9 | 1083 (384) | .[d] | .[d] |
| 6 | 5.8 | 6.6 | 581 (250) | 3.0 | 2.0 |
| 7 | 5.1 | 5.9 | 474 (250) | 2.6 | 1.8 |
| 8 | 4.7 | 4.8 | 653 (314) | 2.8 | 2.1 |
| 9 | 4.7 | 5.7 | 752 (308) | 3.3 | 2.4 |
| 10 | 5.0 | 6.5 | 635 (278) | 2.7 | 2.0 |
| 11 | 4.4 | 5.3 | 793 (281) | 3.4 | 2.6 |
| 12 | 5.7 | 7.1 | 971 (257) | 2.9 | 2.1 |

[a]in water at 40° C. and 20 MHz
[b]concentrations (mM) in parentheses
[c]same concentrations as in osmolality unless otherwise stated
[d]not measured

We claim:

1. A process for the preparation of chelants of formula Vb $$\left( \begin{array}{c} X-(CR^1{}_2)_n-N-(CR^1{}_2)_q \\ | \quad\quad\quad\quad | \\ (CR^1{}_2)_n \quad\quad (CR^1{}_2)_n \\ | \quad\quad\quad\quad | \\ X-\!\!\!+\!\!(CR^1{}_2)_n\!+\!\!\overline{m}X \end{array} \right)_2 D \quad (Vb)$$

wherein each X which may be the same or different is NZ, O or S, at least two Xs being NZ;
each Z is a group $R^1$ or a group $CR^1{}_2Y$, at least one Z on each macrocyclic ring being a group $CR^1{}_2Y$;
each Y is a group $CO_2H$, $PO_3H$, $SO_3H$, $CONR^1{}_2$, $CON(OR^1)R^1$, CNS or $CONR^1NR^1{}_2$;
m is 0 or 1 or 2;
each n is 2 or 3;
q is 1 or 2;
each $R^1$ which may be the same or different is a hydrogen atom or an alkyl group optionally substituted by one or more hydroxy or alkoxy groups;

and D is a bridging group having a molecular weight of less than 1000 joining two macrocyclic rings via at least one amide or ester bond, or salts or metal chelates thereof, said process comprising at least one of the following steps:
(a) reacting a compound of formula Vb wherein at least one group X is a group NH, with a compound of formula VIII $$Lv-R^4 \quad (VIII)$$

wherein Lv is a displaceable leaving group and $R^4$ is a group $CR^1{}_2Y$ or group $R^1$ other than hydrogen;
(b) reacting compounds of formulae X, XI $$\begin{array}{c} X-(CR^1{}_2)_n-N-(CR^1{}_2)_q-COOH \\ | \quad\quad\quad\quad | \\ (CR^1{}_2)_n \quad\quad (CR^1{}_2)_n \\ | \quad\quad\quad\quad | \\ X-\!\!\!+\!\!(CR^1{}_2)_n\!+\!\!\overline{m}X \end{array} \quad (X)$$

$$\begin{array}{c} X-(CR^1{}_2)_n-NH \\ | \quad\quad\quad\quad | \\ (CR^1{}_2)_n \quad\quad (CR^1{}_2)_n \\ | \quad\quad\quad\quad | \\ X-\!\!\!+\!\!(CR^1{}_2)_n\!+\!\!\overline{m}X \end{array} \quad (XI)$$

or a combination thereof, wherein X, $R^1$, m, n, and q are as defined in step (a), with a linker molecule of formula IX $$Lv(CO-X^2)-L^1-(X_2-CO)_tLv \quad (IX)$$

wherein $X^2$ is O or $NR^2$, $R^2$ is a hydrogen atom or a hydroxy, $OR^1$ or $NR^1{}_2$ group or an alkyl group and optionally interrupted by oxygen, sulphur or nitrogen atoms or by carbonyl or aryl groups and optionally substituted by hydroxyl, amine or aryl groups, or $R^2$ contains a functional group for attachment to a biomolecule or macromolecule, or two $R_2$ groups together form a bridging linker group, and $L^1$, which provides a chain or at least two atoms linking two $X^2$ groups or at least one atom linking an $X^2$ group and a $(CR^1{}_2)_q$ moiety, is a straight chain, branched or cyclic alkylene group or a combination of such groups, optionally substituted and optionally being interrupted by oxygen, sulphur or nitrogen atoms or by aryl or carbonyl groups, t is 0 or 1, and each Lv is a displaceable leaving group, one optionally being protected prior to conjugation of the second compound of formula X or XI;

(c) metallating or transmetallating a compound of formula Vb or a chelate thereof;
(d) converting a compound of formula Vb or a chelate thereof into a base or acid addition salt thereof or converting a salt into the free acid or base; and
(e) performing at least one of steps (a) to (c) above using reagents with protected functional groups and subsequently removing the protecting groups.

2. A method of generating enhanced images of the human or non-human animal body, which method comprises administering to said body an effective amount of a diagnostic agent comprising a metal chelate of a compound of formula Vb

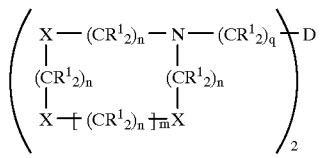

wherein each X which may be the same or different is NZ, O or S, at least two Xs being NZ;
each Z is a group $R^1$ or a group $CR^1_2Y$, at least one Z on each macrocyclic ring being a group $CR^1_2Y$;
each Y is a group $CO_2H$, $PO_3H$, $SO_3H$, $CONR^1_2$, $CON(OR^1)R^1$, CNS or $CONR^1NR^1_2$;
m is 0 or 1 or 2;
each n is 2 or 3;
q is 1 or 2;
each $R^1$ which may be the same or different is a hydrogen atom or an alkyl group optionally substituted by one or more hydroxy or alkoxy group; and
D is a bridging group having a molecular weight of less than 1000 joining two macrocyclic rings via at least one amide or ester bond, or a salt thereof, and
generating an image of at least part of said body to which said chelate distributes, wherein said metal is paramagnetic, radioactive or x-ray opaque.

3. A method of radiotherapy practised on the human or non-human animal body, which method comprises administering to said body an effective amount of a chelate of a radioactive metal species with a chelating agent of formula Vb

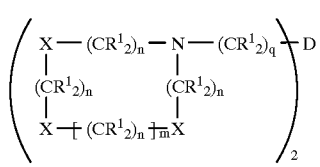

wherein each X which may be the same or different is NZ, O or S, at least two Xs being NZ;
each Z is a group $R^1$ or a group $CR^1_2Y$, at least one Z on each macrocyclic ring being a group $CR^1_2Y$;
each Y is a group $CO_2H$, $PO_3H$, $SO_3H$, $CONR^1_2$, $CON(OR^1)R^1$, CNS or $CONR^1NR^1_2$;
m is 0 or 1 or 2;
each n is 2 or 3;
q is 1 or 2;
each $R^1$ which may be the same or different is a hydrogen atom or an alkyl group optionally substituted by one or more hydroxy or alkoxy group; and
D is a bridging group having a molecular weight of less than 1000 joining two macrocyclic rings via at least one amide or ester bond, or a salt thereof.

4. A method of heavy metal detoxification practised on the human or non-human animal body, which method comprises administering to said body an effective amount of a chelating agent of formula Vb

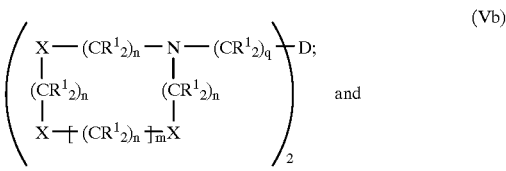

wherein each X which may be the same or different is NZ, O or S, at least two Xs being NZ;
each Z is a group $R^1$ or a group $CR^1_2Y$, at least one Z on each macrocyclic ring being a group $CR^1_2Y$;
each Y is a group $CO_2H$, $PO_3H$, $SO_3H$, $CONR^1_2$, $CON(OR^1)R^1$, CNS or $CONR^1NR^1_2$;
m is 0 or 1 or 2;
each n is 2 or 3;
q is 1 or 2;
each $R^1$ which may be the same or different is a hydrogen atom or an alkyl group optionally substituted by one or more hydroxy or alkoxy group; and
D is a bridging group having a molecular weight of less than 1000 joining two macrocyclic rings via at least one amide or ester bond, or a physiologically tolerable salt thereof.

5. A process for the preparation of metal chelates which process comprises admixing in a solvent a compound of formula

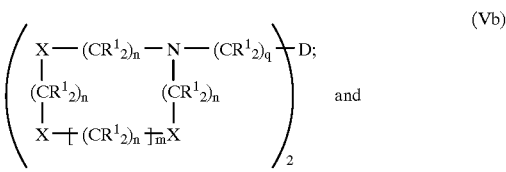

wherein each X which may be the same or different is NZ, O or S, at least two Xs being NZ;
each Z is a group $R^1$ or a group $CR^1_2Y$, at least one Z on each macrocyclic ring being a group $CR^1_2Y$;
each Y is a group $CO_2H$, $PO_3H$, $SO_3H$, $CONR^1_2$, $CON(OR^1)R^1$, CNS or $CONR^1NR^1_2$;
m is 0 or 1 or 2;
each n is 2 or 3;
q is 1 or 2;
each $R^1$ which may be the same or different is a hydrogen atom or an alkyl group optionally substituted by one or more hydroxy or alkoxy group; and
D is a bridging group having a molecular weight of less than 1000 joining two macrocyclic rings via at least one amide or ester bond, or a salt or chelate thereof together with an at least sparingly soluble compound of said metal.

* * * * *